US010738088B2

(12) United States Patent
Vu et al.

(10) Patent No.: US 10,738,088 B2
(45) Date of Patent: Aug. 11, 2020

(54) NON-NATURALLY OCCURRING PORCINE REPRODUCTIVE AND RESPIRATORY SYNDROME VIRUS (PRRSV) AND METHODS OF USING

(71) Applicants: NUtech Ventures, Lincoln, NE (US); The Board of Trustees of the University of Illinois, Urbana, IL (US)

(72) Inventors: Hiep Lai Xuan Vu, Lincoln, NE (US); Fernando Osorio, Lincoln, NE (US); William W. Laegreid, Laramie, WY (US); Asit K. Pattnaik, Lincoln, NE (US); Fangrui Ma, Lincoln, NE (US)

(73) Assignees: NUtech Ventures, Lincoln, NE (US); The Board of Trustees of the University of Illinois, Urbana, IL (US)

( * ) Notice: Subject to any disclaimer, the term of this patent is extended or adjusted under 35 U.S.C. 154(b) by 9 days.

(21) Appl. No.: 16/054,327

(22) Filed: Aug. 3, 2018

(65) Prior Publication Data
US 2019/0048042 A1 Feb. 14, 2019

Related U.S. Application Data

(63) Continuation of application No. 15/127,931, filed as application No. PCT/IB2015/052214 on Mar. 25, 2015, now Pat. No. 10,072,046.

(60) Provisional application No. 61/968,465, filed on Mar. 21, 2014.

(51) Int. Cl.
| *C07K 14/005* | (2006.01) |
| *A61K 39/12* | (2006.01) |
| *C12N 7/00* | (2006.01) |
| *A61K 39/00* | (2006.01) |

(52) U.S. Cl.
CPC ............ *C07K 14/005* (2013.01); *A61K 39/12* (2013.01); *C12N 7/00* (2013.01); *A61K 2039/552* (2013.01); *C12N 2770/10021* (2013.01); *C12N 2770/10022* (2013.01); *C12N 2770/10034* (2013.01)

(58) Field of Classification Search
None
See application file for complete search history.

(56) References Cited

U.S. PATENT DOCUMENTS

| 7,608,272 B2 | 10/2009 | Ansari et al. | |
| 2002/0012670 A1 | 1/2002 | Elbers et al. | |
| 2008/0019912 A1 | 1/2008 | Harris | |
| 2008/0233083 A1 | 9/2008 | Ansari et al. | |
| 2011/0104201 A1 | 5/2011 | Mengeling et al. | |
| 2013/0028931 A1* | 1/2013 | Gallei ................. | C07K 14/005 424/204.1 |
| 2017/0198016 A1 | 7/2017 | Vu | |

FOREIGN PATENT DOCUMENTS

| RU | 2220978 | 1/2004 |
| WO | WO 2012063212 | 5/2012 |

OTHER PUBLICATIONS

Alignment of SEQ ID No. 2 with GenEmbl database access No. EF532801 by Murtaugh et al 2007.*
Alignment of SEQ ID No. 2 with Geneseq database access No. ADM36185 by Mengeling et al in USPgPub 2003119170 Jun. 2003.*
Alignment of SEQ ID No. 3 with Geneseq database access No. BAK06098 by Gallei in USPgPub 20130028931.*
Alignment of SEQ ID No. 3 with UniProt database access No. B5A487_PRRSV by Cai et al 2008.*
Alignment of SEQ ID No. 3 with UniProt database access No. K7WJI8_PRRSV Wang in J of Vet Sci 2009.*
Alignment of SEQ ID No. 3 with UniProt database access No. Q6QDR1_PRRSV by Truong et al 2004.*
Rascon-Castelo et al. (Viruses. 2015; 7: 873-886).*
Amonsin et al., "Comparative Analysis of Complete Nucleotide Sequence of Porcine Reproductive and Respiratory Syndrome Virus (PRRSV) Isolates in Thailand (US and EU genotypes)," Virology Journal, Sep. 2009, 6: 1-10.
An et al., "Identification of a Novel B Cell Epitope on the Nucleocapsid Protein of Porcine Reproductive and Respiratory Syndrome Virus by Phage Display," Virus Genes, Aug. 2005, 31: 81-87.
Database Accession No. BAK27904 & WO 2013/017570, "PRRSSV VR2332 nspl alpha protein," Apr. 11, 2013, 1 page.
Database Accession No. JX294618, "Porcine reproductive and respiratory syndrome virus isolate 21599-00 RNA-dependent RNA polymerase gene, partial cds," Jul. 18, 2012, 1 page.
Database Accession No. JX294702, "Porcine reproductive and respiratory syndrome virus isolate 5424-00 nsplO gene, partial cds," Jul. 18, 2012, 1 page.
Database Accession No. NP 740598, "nsp4 (3CLSP) [Porcine reproductive and respiratory syndrome virus]," Nov. 2012, 2 pages.
European Search Report in Application No. 15765669.5, dated Dec. 1, 2017, 17 pages.
Extended European Search Report in Application No. 15765669.5, dated Mar. 7, 2018, 13 pages.
GenBank Accession No. JB398242.1, "Sequence 4 from patent WO2012063212," dated Oct. 2, 2013, 4 pages.
GenBank Accession No. AR908837.1, "Sequence 2 from U.S. Pat. No. 7,081,342," dated Aug. 11, 2006, 4 pages.
GenBank Accession No. AR908839.1, "Sequence 4 from U.S. Pat. No. 7,081,342," dated Aug. 11, 2006, 4 pages.
GenBank Accession No. GP721394.1, "Sequence 16 from U.S. Pat. No. 7,608,272," dated Dec. 14, 2009, 4 pages.
GenBank Accession No. JB398243.1, "Sequence 5 from patent WO2012063212," dated Oct. 2, 2013, 4 pages.

(Continued)

*Primary Examiner* — Shanon A. Foley
(74) *Attorney, Agent, or Firm* — Fish & Richardson P.C.

(57) ABSTRACT

A non-naturally occurring porcine reproductive and respiratory syndrome virus (PRRSV) is provided herein, and methods of making and using the non-naturally occurring PRRSV also are provided.

11 Claims, 5 Drawing Sheets

Specification includes a Sequence Listing.

(56) References Cited

OTHER PUBLICATIONS

International Preliminary Report on Patentability in International Application No. PCT/IB2015/052214, dated Sep. 21, 2016, 9 pages.
International Search Report and Written Opinion in International Application No. PCT/IB2015/052214, dated Aug. 19, 2015, 16 pages.
Nan et al. (Frontiers in Microbiology. Aug. 2017; 8 (1635): 1-17).
Office Action in RU2016141287, dated Jun. 7, 2018, 16 pages (with English translation).
Sun et al. (Vaccine. 2018; 36: 66-73).
Vu et al. (Journal of Virology. Sep. 2015; 89(23): 12070-12083).
Vu et al., "A Synthetic Porcine Reproductive and Respiratory Syndrome Virus Strain Confers Unprecedented Levels of Heterologous Protection," Journals of Virology, Dec. 2015, 89: 12071-12083.
Vu et al., "Development of a synthetic porcine reproductive and respiratory syndrome virus strain that confers broader cross-protection," NC229 Meeting, Dec. 2014, 11 pages.
Vu et al., "Supplemental Material: A Synthetic Porcine Reproductive and Respiratory Syndrome Virus Strain Confers Unprecedented Levels of Heterologous Protection," Journals of Virology, Dec. 2015, 2 pages.
Brockmeier et al., "Genomic sequence and virulence comparison of four Type porcine reproductive and respiratory virus strains," Virus Research, 2012, 169(1):212-221.
PH Subsequent Substantive Examination Report in PH Appln. No. 1-2016-501854, dated Feb. 7, 2020, 5 pages.

\* cited by examiner

NON-NATURALLY OCCURRING PORCINE REPRODUCTIVE AND RESPIRATORY SYNDROME VIRUS (PRRSV) AND METHODS OF USING

CROSS REFERENCE TO RELATED APPLICATIONS

This application is a continuation application of U.S. patent application Ser. No. 15/127,931 filed on Sep. 21, 2016, which is a U.S. National Application from PCT Application No. PCT/IB2015/052214 filed on Mar. 25, 2015, which claims the benefit of priority under 35 U.S.C. § 119(e) to U.S. Application No. 61/968,465, filed Mar. 21, 2014.

FEDERALLY SPONSORED RESEARCH OR DEVELOPMENT

This invention was made with government support under 2013-31100-06031, 2012-31100-06031, and 2008-5562-19132 awarded by United States Department of Agriculture, National Institute of Food and Agriculture. The government has certain rights in the invention.

TECHNICAL FIELD

This disclosure generally relates to a non-naturally occurring porcine reproductive and respiratory syndrome virus (PRRSV) and methods of using.

BACKGROUND

Current porcine reproductive and respiratory syndrome virus (PRRSV) vaccines are not adequately effective for control and eradication of porcine reproductive and respiratory syndrome (PRRS). The main limitation of the current PRRSV vaccines is their sub-optimal coverage against divergent PRRSV strains. Thus far, all commercial PRRSV vaccines are formulated using natural PRRSV strains, but the substantial genetic variation among the PRRSV strains is the biggest obstacle for the development of a broadly protective PRRSV vaccine.

SUMMARY

This disclosure provides a non-naturally occurring porcine reproductive and respiratory syndrome virus (PRRSV) and methods of making and using the non-naturally occurring PRRSV.

A PRRSV-CON nucleic acid is provided, where the nucleic acid has at least 50% sequence identity (e.g., at least 75%, at least 95%, or at least 99% sequence identity) to SEQ ID NO:1. In some embodiment, the nucleic acid has the sequence shown in SEQ ID NO:1. A virus particle comprising the PPRSV-CON nucleic acid described herein. A composition comprising the PPRSV-CON nucleic acid described herein and a pharmaceutically acceptable carrier. A composition comprising the virus particle described herein and a pharmaceutically acceptable carrier. The compositions described herein, further comprising an adjuvant.

A PRRSV-CON nucleic acid also is provided, where the nucleic acid has at least 95% (e.g., at least 99%) sequence identity to a sequence selected from the group consisting of SEQ ID NO:2, 4, 6, 8, 10, 12, 14, 16, 18, 20, 22, 24, 26, 28, 30, 32, 34, 36, 38, 40, and 42. In some embodiments, the nucleic acid has a sequence selected from the group consisting of SEQ ID NO:2, 4, 6, 8, 10, 12, 14, 16, 18, 20, 22, 24, 26, 28, 30, 32, 34, 36, 38, 40, and 42. In some embodiments, the nucleic acid encodes, respectively, a polypeptide having an amino acid sequence selected from the group consisting of SEQ ID NO:3, 5, 7, 9, 11, 13, 15, 17, 19, 21, 23, 25, 27, 29, 31, 33, 35, 37, 39, 41 and 43. A virus particle comprising the PPRSV-CON nucleic acid described herein. A composition comprising the nucleic acid described herein and a pharmaceutically acceptable carrier. A composition comprising the virus particle described herein and a pharmaceutically acceptable carrier. The composition described herein, further comprising an adjuvant.

A PRRSV-CON polypeptide is provided, where the polypeptide has at least 95% (e.g., at least 99%) sequence identity to a sequence selected from the group consisting of SEQ ID NO:3, 5, 7, 9, 11, 13, 15, 17, 19, 21, 23, 25, 27, 29, 31, 33, 35, 37, 39, 41 and 43. In some embodiments, the polypeptide has a sequence selected from the group consisting of SEQ ID NO:3, 5, 7, 9, 11, 13, 15, 17, 19, 21, 23, 25, 27, 29, 31, 33, 35, 37, 39, 41 and 43. In some embodiments, the polypeptide is encoded by a nucleic acid, respectively, having a sequence selected from the group consisting of SEQ ID NOs:2, 4, 6, 8, 10, 12, 14, 16, 18, 20, 22, 24, 26, 28, 30, 32, 34, 36, 38, 40, or 42. A virus particle comprising the PPRSV-CON polypeptide described herein. A composition comprising the polypeptide described herein and a pharmaceutically acceptable carrier. A composition comprising the virus particle described herein and a pharmaceutically acceptable carrier. The composition described herein, further comprising an adjuvant.

A method for eliciting an immune response to PPRSV in a porcine is provided. Such a method typically includes administering, to a porcine: (i) an effective amount of any of the nucleic acids described herein; (ii) an effective amount of any of the polypeptides described herein; (iii) an effective amount of any of the virus particles described herein; or (iv) an effective amount of any of the compositions described herein. Representative routes of administration include, without limitation, intramuscularly, intraperitoneally, and orally.

A method for treating or preventing PPRS in a porcine is provided. Such a method typically includes administering, to a porcine: (i) an effective amount of any of the nucleic acids described herein; (ii) an effective amount of any of the polypeptides described herein; (iii) an effective amount of any of the virus particles described herein; or (iv) an effective amount of any of the compositions described herein. Representative routes of administration include, without limitation, intramuscularly, intraperitoneally, and orally.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1, Panel (A) is a phylogenetic tree constructed from a set of 60 PRRSV full-genome sequences. These 60

PRRSV genomes are classified into 4 sub-groups. The locations of the viruses involved in the cross-protection experiments are indicated by the arrows. FIG. 1, Panel (B) is a graph showing the genetic distances among natural PRRSV strains and the genetic distance from the PRRSV-CON described herein to the natural PRRSV strains. The lower and upper boundaries of the box indicate the 25th and 75th percentile respectively. The solid line within the box represents the median. Whiskers above and below the box indicate the minimum and maximum of the data.

FIG. 2 shows the generation and characterization of the PRRSV-CON virus. Panel (A) is a schematic showing the strategy to construct the PRRSV-CON full-genome cDNA clone. The upper half of Panel (A) depicts the schematic representation of the viral genome, together with the unique restriction enzyme sites used for cloning purposes. The horizontal black lines, with the letters A-D on top, represent the DNA fragments that were synthesized. The numbers inside the parenthesis below the lines indicate the length (in nucleotides) of each corresponding fragments. ΦT7 represents the T7 RNA polymerase promoter. Individual DNA fragments of the genome were sequentially inserted into the shuttle vector (shown in the lower half of Panel (A)) in the order of fragment A to fragment D. Panel (B) are photographs showing the reactivity of the indicated viruses with different PRRSV-specific monoclonal antibodies. MARC-145 cells were mock infected or infected with PRRSV-CON or PRRSV wild type strain, FL12. At 48 hours post-infection, the cells were stained with antibodies specific to the viral nucleocapsid protein (N protein; bottom row of photographs) or to the viral nonstructural protein 1 beta (nsp1b; top row of photographs). Panel (C) shows the plaque morphology of the viruses in MARC-145 cells. Panel (D) shows a multiple step growth curve. MARC-145 cells were infected with the indicated viruses at a multiplicity of infection (MOI) of 0.01. At different timepoints post-infection (p.i.), culture supernatant was collected and viral titer was determined by titration on MARC-145 cells.

FIG. 5 is data demonstrating cross-protection against PRRSV strain, 16244B. Panel (A) shows the average daily weight gain (ADWG) within 15 days after challenge-infection. Panel (B) shows the viremia levels after challenge infection determined by a commercial, universal RT-qPCR (Tetracore Inc., Rockville, Md.). Panel (C) shows total viral RNA levels in different tissues collected at 15 days post-challenge as determined by a commercial, universal RT-qPCR (Tetracore Inc., Rockville, Md.). Panel (D) shows the 16244B-specific RNA levels as determined by a differential RT-qPCR developed in-house.

DETAILED DESCRIPTION

Figure 3:
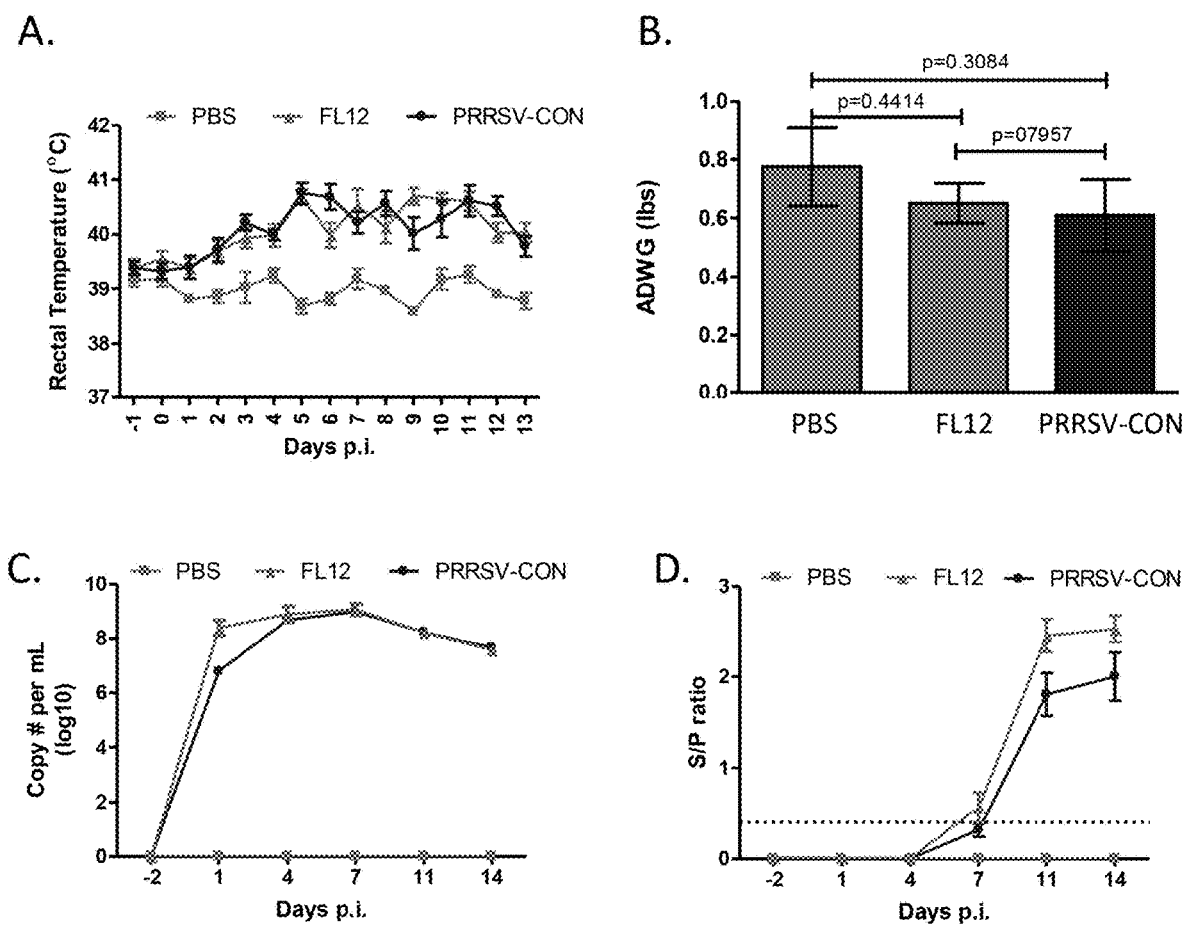
FIG. 3 is data demonstrating replication of the PRRSV-CON in pigs. Panel (A) shows the rectal temperature measured daily from 1 day before infection to 13 days post-infection (days p.i.). Panel (B) shows the average daily weight gain (ADWG) within 14 days after inoculation. Panel (C) shows the viremia levels, determined by a commercial, universal RT-qPCR (Tatracore Inc., Rockville, Md.). Panel (D) shows the levels of antibody response after inoculation, determined by IDEXX ELISA; the horizontal dotted line indicates the cut-off of the assay.

A non-naturally occurring porcine reproductive and respiratory syndrome virus (PRRSV) genome was designed using a large set of genomic sequences of PRRSV isolates, which represents the widest genetic diversity of PRRSV strains circulating in U.S. swine herds. The non-naturally occurring PRRSV genome was designed so that it has a high degree of genetic similarity to the PRRSV field-isolates studied when compared to any single, naturally occurring PRRSV strain.

Porcine reproductive and respiratory syndrome (PRRS) is one of the most economically important diseases in swine. Clinical signs of the disease include reproductive failure in pregnant sows and respiratory disorder in young pigs. The disease is more severe when animals are co-infected with other pathogens. The annual loss to the US swine industry was estimated to be about $560 million in 2005 and about $640 million in 2011.

The causative agent of PRRS is an RNA virus named PRRS virus (PRRSV). PRRSV is classified into two major genotypes: European (Type 1) and North American (Type 2). There is limited cross-protection between these two genotypes. Considerable genetic variation exists among PRRSV isolates within each of these genotypes. Importantly, genetic divergence has been shown to occur when a PRRSV strain is serially passed from pig to pig. This leads to co-circulation of multiple PRRSV variants within one herd or even within one animal that is persistently infected with PRRSV.

PRRSV vaccines have been in use since 1994. There are two types of PRRSV vaccines currently available in the market; modified-live and inactivated vaccines. In addition, several subunit vaccines against PRRSV are being tested in different laboratories worldwide, but none have been licensed for clinical application. Currently, PRRSV vaccines are prepared using naturally occurring PRRSV strains as the vaccine immunogens. The current PRRSV vaccines are not adequately effective for control and eradication of PRRS; they provide acceptable levels of homologous protection but they fail to provide consistent heterologous cross-protection. Extensive genetic diversity among PRRSV isolates is the main reason behind the sub-optimal heterologous protection of the current PRRSV vaccines.

The non-naturally occurring PRRSV-CON described herein confers superior cross-protective against different heterologous PRRSV strains, as compared to the PRRSV wild type strain FL12. Thus, the PRRSV-CON described herein can be used to formulate a universal PRRSV vaccine. In addition, the PRRSV-CON described herein provides an important tool to study the mechanism of heterologous protection against divergent PRRSV strains.

Nucleic Acids and Polypeptides

The PRRSV genome encodes at least 22 proteins; 14 non-structural proteins and 8 structural proteins. A nucleic acid is provided herein that encodes for a non-naturally occurring PRRSV. See SEQ ID NO:1 for the genomic sequence of PRRSV-CON. The non-naturally occurring PRRSV described herein possesses the highest degree of genetic identity with the naturally occurring PRRSV isolates. The PRRSV-CON genomic nucleic acid provided herein (i.e., SEQ ID NO:1) encodes for a number of different polypeptides. For example, the nucleic acid sequence shown in SEQ ID NO:2 encodes for the polypeptide sequence having the amino acid sequence shown in SEQ ID NO:3; the nucleic acid sequence shown in SEQ ID NO:4 encodes for the polypeptide sequence having the amino acid sequence shown in SEQ ID NO:5; the nucleic acid sequence shown in SEQ ID NO:6 encodes for the polypeptide sequence having the amino acid sequence shown in SEQ ID NO:7; the nucleic acid sequence shown in SEQ ID NO:8 encodes for the polypeptide sequence having the amino acid sequence shown in SEQ ID NO:9; the nucleic acid sequence shown in SEQ ID NO:10 encodes for the polypeptide sequence having the amino acid sequence shown in SEQ ID NO:11; the nucleic acid sequence shown in SEQ ID NO:12 encodes for the polypeptide sequence having the amino acid sequence shown in SEQ ID NO:13; the nucleic acid sequence shown in SEQ ID NO:14 encodes for the polypeptide sequence having the amino acid sequence shown in SEQ ID NO:15; the nucleic acid sequence shown in SEQ ID NO:16 encodes for the polypeptide sequence having the amino acid sequence shown in SEQ ID NO:17; the nucleic acid sequence shown in SEQ ID NO:18 encodes for the polypeptide sequence having the amino acid sequence shown in SEQ ID NO:19; the nucleic acid sequence shown in SEQ ID NO:20 encodes for the polypeptide sequence having the amino acid sequence shown in SEQ ID NO:21; the nucleic acid sequence shown in SEQ ID NO:22 encodes for the polypeptide sequence having the amino acid sequence shown in SEQ ID NO:23; the nucleic acid sequence shown in SEQ ID NO:24 encodes for the polypeptide sequence having the amino acid sequence shown in SEQ ID NO:25; the nucleic acid sequence shown in SEQ ID NO:26 encodes for the polypeptide sequence having the amino acid sequence shown in SEQ ID NO:27; the nucleic acid sequence shown in SEQ ID NO:28 encodes for the polypeptide sequence having the amino acid sequence shown in SEQ ID NO:29; the nucleic acid sequence shown in SEQ ID NO:30 encodes for the polypeptide sequence having the amino acid sequence shown in SEQ ID NO:31; the nucleic acid sequence shown in SEQ ID NO:32 encodes for the polypeptide sequence having the amino acid sequence shown in SEQ ID NO:33; the nucleic acid sequence shown in SEQ ID NO:34 encodes for the polypeptide sequence having the amino acid sequence shown in SEQ ID NO:35; the nucleic acid sequence shown in SEQ ID NO:36 encodes for the polypeptide sequence having the amino acid sequence shown in SEQ ID NO:37; the nucleic acid sequence shown in SEQ ID NO:38 encodes for the polypeptide sequence having the amino acid sequence shown in SEQ ID NO:39; the nucleic acid sequence shown in SEQ ID NO:40 encodes for the polypeptide sequence having the amino acid sequence shown in SEQ ID NO:41; and the nucleic acid sequence shown in SEQ ID NO:42 encodes for the polypeptide sequence having the amino acid sequence shown in SEQ ID NO:43.

As used herein, nucleic acids can include DNA and RNA, and includes nucleic acids that contain one or more nucleotide analogs or backbone modifications. A nucleic acid can be single stranded or double stranded, which usually depends upon its intended use. Nucleic acids and polypeptides that differ from SEQ ID NOs:1-43 also are provided. Nucleic acids that differ in sequence from SEQ ID NO:1 or any of SEQ ID NOs:2, 4, 6, 8, 10, 12, 14, 16, 18, 20, 22, 24, 26, 28, 30, 32, 34, 36, 38, 40, or 42 can have at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NO:1 or any of SEQ ID NOs:2, 4, 6, 8, 10, 12, 14, 16, 18, 20, 22, 24, 26, 28, 30, 32, 34, 36, 38, 40, or 42. Polypeptides that differ in sequence from any of SEQ ID NOs:3, 5, 7, 9, 11, 13, 15, 17, 19, 21, 23, 25, 27, 29, 31, 33, 35, 37, 39, 41 or 43, can have at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to any of SEQ ID NOs:3, 5, 7, 9, 11, 13, 15, 17, 19, 21, 23, 25, 27, 29, 31, 33, 35, 37, 39, 41 or 43.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13):3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NO:1 or any of SEQ ID NOs:2, 4, 6, 8, 10, 12, 14, 16, 18, 20, 22, 24, 26, 28, 30, 32, 34, 36, 38, 40, or 42), thereby leading to changes in the amino acid sequence of the encoded polypeptide (e.g., SEQ ID NOs:3, 5, 7, 9, 11, 13, 15, 17, 19, 21, 23, 25, 27, 29, 31, 33, 35, 37, 39, 41 or 43). For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)) Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame). Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Methods of Making and Using a PRRSV-CON Virus Particle

Methods of constructing a virus particle from a PRRSV-CON nucleic acid are known in the art and are described herein. As demonstrated herein, the PRRSV-CON described herein self-assembles into particles when appropriately expressed. The PRRSV-CON can be expressed in vitro or in vivo, for example, in a host cell. In some embodiments, a host cell can be transfected with the PRRSV-CON nucleic acid, or a host cell can be infected with a PRRSV-CON virus particle. Host cells can be, without limitation, porcine cells (e.g., porcine alveolar macrophage) or African green monkey kidney-derived cells (e.g., MARC-145). Virus particles can be isolated, for example, by ultracentrifugation.

The PRRSV-CON nucleic acids, polypeptides or virus particles described herein can be used to generate, enhance or modulate the immune response of a porcine. Such methods typically include administering a PRRSV-CON nucleic acid, polypeptide or virus particle described herein to a porcine in an amount sufficient to generate an immune response. As used herein, an "immune response" refers to the reaction elicited in an individual following administration of a PRRSV-CON nucleic acid, polypeptide or virus particle as described herein. Immune responses can include, for example, an antibody response or a cellular response (e.g., a cytotoxic T-cell response). A PRRSV-CON nucleic acid, polypeptide or virus particle can be used to prevent PRRS in porcine, e.g., as a prophylactic vaccine, or to establish or enhance immunity to PRRS in a healthy individual prior to exposure or contraction of PRRS, thus preventing the disease or reducing the severity of disease symptoms.

Methods for administering a PRRSV-CON nucleic acid, polypeptide or virus particle to a porcine include, without limitation, intramuscular (i.m.), subcutaneous (s.c.), or intrapulmonary routes. Methods for administering a PRRSV-CON nucleic acid, polypeptide or virus particle to a porcine also include, without limitation, intratracheal, transdermal, intraocular, intranasal, inhalation, intracavity, and intravenous (i.v.) administration.

Determining an effective amount of a PRRSV-CON nucleic acid, polypeptide or virus particle depends upon a number of factors including, for example, whether the antigen is being expressed or administered directly, the age and weight of the subject, the precise condition requiring treatment and its severity, and the route of administration. Based on the above factors, determining the amount and the dosing (e.g., the number of doses and the timing of doses) are within the level of skill of an ordinary artisan.

A composition can include a PRRSV-CON nucleic acid, polypeptide or virus particle as described herein and a pharmaceutically acceptable carrier. Pharmaceutically acceptable carriers are known in the art and include, for example, buffers (e.g., phosphate buffered saline (PBS), normal saline, Tris buffer, and sodium phosphate) or diluents. The compositions described herein can be formulated as an aqueous solution, or as an emulsion, gel, solution, suspension, or powder. See, for example, Remington's Pharmaceutical Sciences, 16th Ed., Osol, ed., Mack Publishing Co., Easton, Pa. (1980), and Remington's Pharmaceutical Sciences, 19th Ed., Gennaro, ed., Mack Publishing Co., Easton, Pa. (1995). In addition to a pharmaceutically acceptable carrier, the compositions described herein also can include binders, stabilizers, preservatives, salts, excipients, delivery vehicles and/or auxiliary agents.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Computational Design of the Artificial PRRSV-CON Genome

Figure 1:
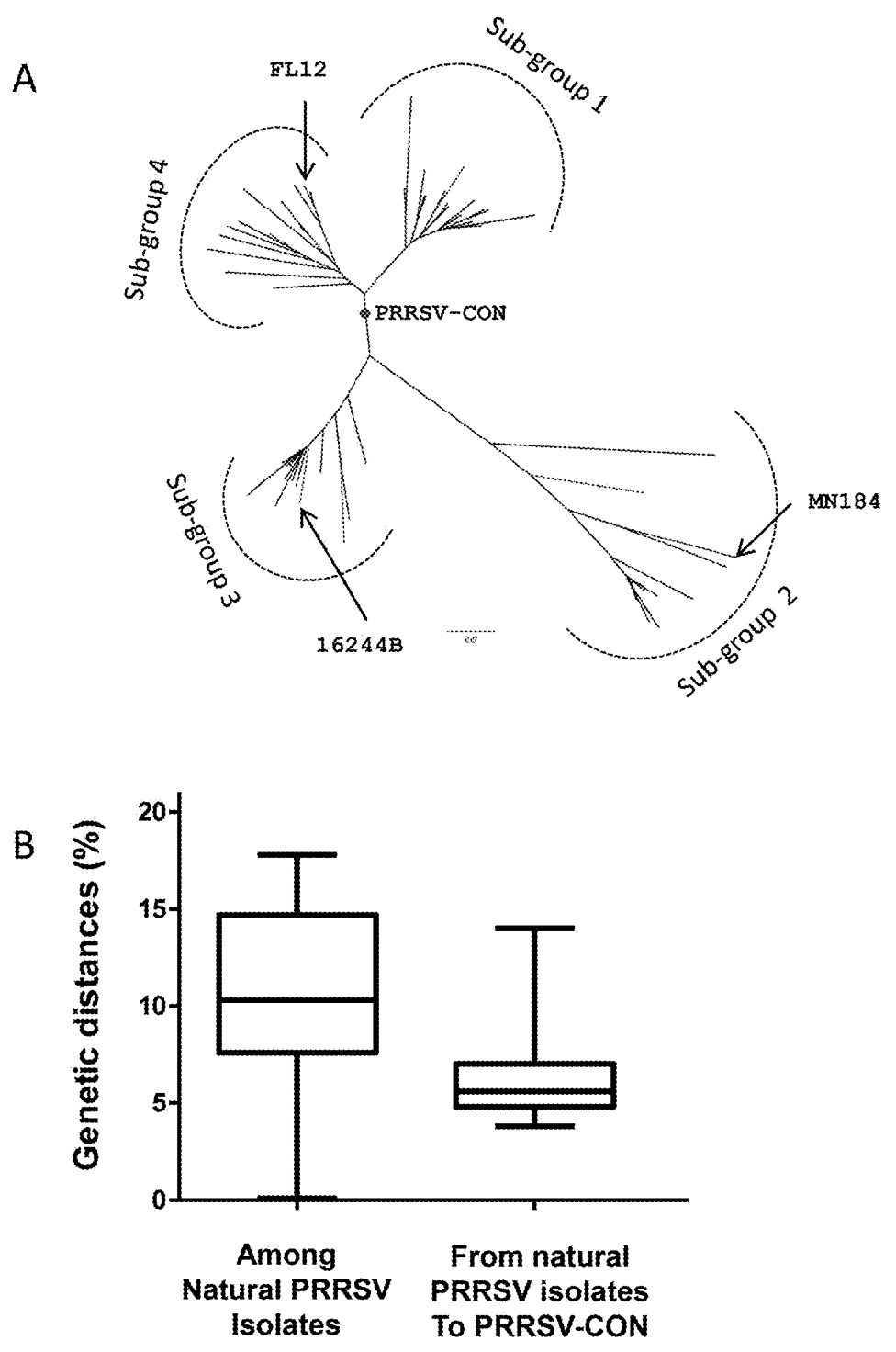

Full-genome sequences of 64 PRRSV isolates originating from the Midwestern states (Iowa, Nebraska and Illinois) of the U.S. were sequenced using the Roche 454-GS-FLX sequencing technology. In addition, more than 20 full-genome sequences of PRRSV isolates originating from the U.S. were collected from GenBank. After removing redundant sequences, a final set of 60 full-genome sequences of PRRSV was attained. The 60 PRRSV full-genome sequences were aligned using the MUSCLE program (Edgar RC, 2004, BMC Bioinform., 5:113). After that, a consensus genome sequence (PRRSV-CON) was generated by selecting the most common nucleotide found at each position of the viral genome, using the Jalview program. Phylogenetic analysis shows that the PRRSV-CON genome locates right at the center of the phylogenetic tree. See FIG. 1A. Consequently, the pairwise genetic distance from PRRSV-CON to the naturally occurring PRRSV strains is significantly shorter than the distance from any one naturally occurring PRRSV strains to each other (p<0.0001). See FIG. 1B.

Example 2—Generation of an Infectious PRRSV-CON Virus

It is generally difficult to accurately determine the sequence at 5' and 3' ends of a viral genome. Thus, we realized that the sequences at the 5' and 3' untranslated regions (UTRs) of the naturally occurring PRRSV genomes analyzed in Example 1 may not be accurate. To increase the change of recovering infectious virus, we replaced the 5' and 3'UTRs of the PRRSV-CON genome with the 5' and 3' UTRs of the infectious cDNA clone FL12 (Truong et al., 2004, Virology, 325:308-19). Four DNA fragments, designated A-D, encompassing the entire PRRSV-CON genome, were chemically synthesized by Genscript (Piscataway, N.J.). Each DNA fragment was flanked by a pair of restriction enzyme sites to facilitate the cloning purposes. The T7 RNA polymerase promoter sequence was incorporated into fragment D, preceding the viral 5'end, to facilitate the in vitro transcription of the viral genome. See FIG. 2A. Individual DNA fragments were sequentially cloned into the shuttle vector that carries the corresponding restriction enzyme site, following the order from fragment A to fragment D. Once the full-length PRRSV-CON cDNA clone was generated, standard reverse genetics techniques were applied to recover viable PRRSV-CON viruses.

Briefly, the plasmid containing full-length cDNA genome of PRRSV-CON was digested with AclI for linearization. The purified, linear DNA fragment was used as the template for an in vitro transcription reaction using the mMES-SAGEmMACHINE Ultra T7 kit (Ambion, Austin, Tex.) to generate full genome viral RNA transcripts. After that, about 5 μg of the full-genome RNA transcripts were transfected into MARC-145 cells cultured in a 6-well plate, using the TransIT®-mRNA Transfection Kit (Mirus Bio, Madison, Wis.). Transfected cells were cultured in DMEM containing 10% FBS at 37° C., 5% CO2 for up to 6 days. Typically, cytopathic effect (CPE) was observed between day 4 and day 6 after transfection. When clear CPE was observed, culture supernatant containing the rescued virus was collected and stored in 0.5 mL aliquots in a 80° C. freezer. See, Truong et al. (2004, supra)

Example 3—In Vitro Characterization of the PRRSV-CON Virus

To study the reactivity with different PRRSV-specific monoclonal antibodies, MARC-145 cells were mock infected or infected with the PRRSV-CON virus or the PRRSV strain FL12. At 48 hours post-infection (p.i.), the cells were immunostained with antibodies specific to the viral nucleocapsid (N) protein or the viral nonstructural protein 1 beta (nsp1b). To study the growth kinetics of the viruses in cell culture, MARC-145 cells were infected with the PRRSV-CON or FL12 at a multiplicity of infection (MOI) of 0.01. At different time-points p.i., culture supernatant was collected and viral titers were determined by titration in MARC-145 cells.

Figure 2:
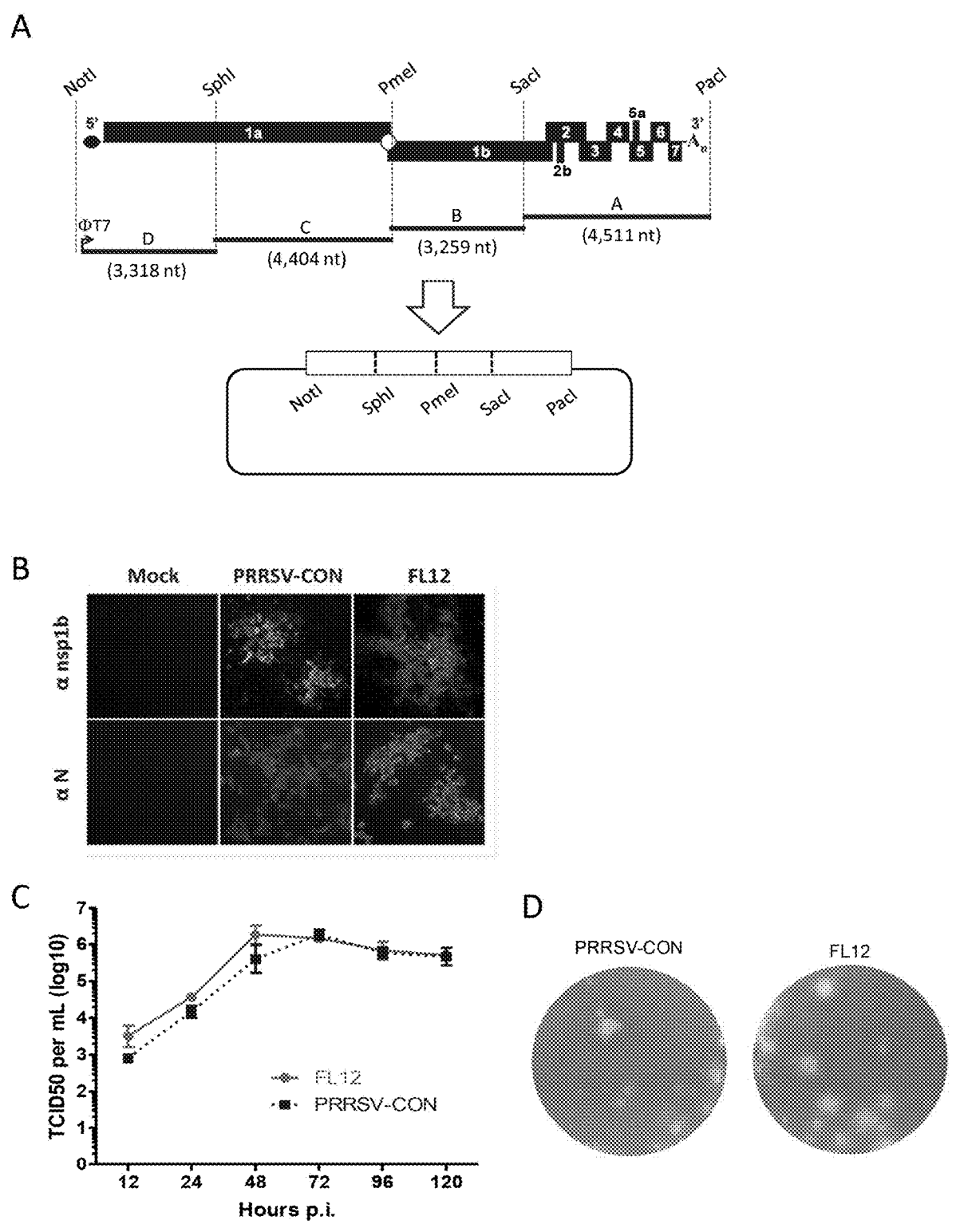

The PRRSV-CON virus displays typical in vitro characterizations of a naturally occurring PRRSV strain. It reacts with different PRRSV-specific monoclonal antibodies including antibodies against nsp1-betta and N protein (FIG. 2B). It replicates efficiently in cell culture (FIG. 2C), and it is able to form clear and distinct plaque morphology (FIG. 3D).

Example 4—the PRRSV-CON Virus can Infect Pigs as Efficiently as the Natural PRRSV Strain A total of 18 PRRSV-seronegative, 3 week-old pigs were purchased from the University of Nebraska research farm. The pigs were randomly assigned into 3 experimental groups; each group was housed in a separate room in the Biosecurity Level-2 Animal Research Facilities at UNL, following the regulations established by the Institutional Animal Care and Use Committee. Pigs in group 1 were injected with PBS to act as the control. Pigs in groups 2 and 3 were inoculated intramuscularly with $10^{5.0}$ $TCID_{50}$ of PRRSV-CON and PRRSV strain FL12, respectively. The wild-type PRRSV strain, FL12, was included into this study for comparison purposes. The results are shown in FIG. 3. After infection, both of the PRRSV-CON and FL12-inoculated groups displayed significantly higher temperature than PBS-group (FIG. 3A), but there was no difference in temperature between PRRSV-CON-inoculated group and the FL12-inoculated group. Average daily weight gain (ADWG) was measured for each individual pig during the period of 14 days after infection. No statistical difference was observed among the three treatment groups, although pigs in the PRRSV-CON-inoculated group and the FL12-inoculated group tended to have lower ADWG than the PBS group (FIG. 3B). Viremia levels of the PRRSV-CON- and FL12-inoculated groups were almost identical (FIG. 3C). All pigs in the PRRSV-CON- and FL12-inoculated groups were seroconverted by 11 days p.i. The level of antibody response in the PRRSV-CON-inoculated group was slightly lower than that of the FL12-inoculated group (FIG. 3D). These results demonstrate that the PRRSV-CON can infect the natural host (i.e., pigs) as efficiently as the PRRSV strain, FL12.

Example 5—Evaluation of the Level of Cross-Protection Against PRRSV Strain MN-184

Materials and Methods

A total of 18 PRRSV-seronegative, 3 week-old pigs were purchased from the University of Nebraska research farm. The pigs were randomly assigned into 3 experimental groups; each group was housed in a separate room in the Biosecurity Level-2 Animal Research Facilities at UNL, following the regulations established by the Institutional Animal Care and Use Committee. Group 1 was injected with PBS and served as the non-immunization control. Group 2 was immunized by infection, intramuscularly, with PRRSV-CON at the dose of $10^{4.0}$ $TCID_{50}$ per pig. Group 3 was immunized by infection, intramuscularly, with the wild-type PRRSV strain, FL12, at the dose of $10^{4.0}$ $TCID_{50}$ per pig. See Table 1. At 53 days post-infection (p.i.), all control and immunized pigs were challenged, intramuscularly, with PRRSV strain MN-184 at a dose of $10^{5.0}$ $TCID_{50}$. Parameters used to evaluate protection by immunization with the PRRSV-CON virus included viremia and viral load in several different tissues as well as growth performance.

TABLE 1

Experimental Design to Evaluate Level of Cross-Protection Against PRRSV Strain MN-184

| Groups | Immunized with | Challenged with |
|---|---|---|
| 1 (n = 6) | PBS | MN-184 |
| 2 (n = 6) | PRRSV-CON | (Sub-group 2) |
| 3 (n = 6) | PRRSV strain FL12 | |

To measure growth performance, each pig was weighed right before challenge infection and 15 days post-challenge.

Body weight was recorded in pounds. Average daily weight gain (ADWG) was calculated for the period of 15 days post-challenge.

To quantitate levels of viremia after challenge infection, blood samples were taken before challenge and at days 1, 4, 7, 10, and 15 post-challenge. Serum samples were extracted from each individual blood samples and stored in a −80° C. freezer. Viremia levels were quantitated by the Animal Disease Research and Diagnostic Laboratory, South Dakota State University, using the universal RT-qPCR kit (Tetracore Inc., Rockville, Md.). Results were reported as log 10 copy/mL. For statistical purposes, samples that had undetected level of viral RNA were assigned a value of 0 log 10 copy/mL.

To quantitate levels of viral load in tissues, pigs were humanely sacrificed and necropsied on day 15 post-challenge. Samples of tonsil, lung, mediastinal lymph node and inguinal lymph node were obtained and kept individually in Whirl-Pak® bags. The samples were snap-frozen in liquid nitrogen right after collection. After that, they were stored in a −80° C. freezer. To extract RNA, tissue samples were homogenized in Trizol reagent (Life Technologies, Carlsbad, Calif.) with a ratio of 300 mg tissue in 3 mL Trizol reagent. Total RNA was extracted using the RNeasy Mini Kit (Qiagen, Valencia, Calif.) following the manufacturer's instruction. RNA concentration was quantitated by the NanoDrop® ND-1000 (NanoDrop Technologies, Inc., Wilmington, Del.) and adjusted to a final concentration of 200 ng/4.

It has been well characterized that PRRSV can colonize and persist in lymphoid tissues of infected pigs up to 150 days post-infection. In these experiments, the tissue viral load was evaluated at 15 days post-challenge, which corresponds to 67 days after the primary infection. At that time, it is likely that the pigs in the PRRSV-CON and FL12 groups still contained residual virus of the primary infection. Therefore, we used two different RT-PCR kits to quantify the viral RNA load in tissues: (i) the commercial RT-qPCR kit (Tetracore Inc., Rockville, Md.) that detects total viral RNA resulting from both the primary infection and the challenge infection, and (ii) the differential RT-PCR developed in-house that selectively detects only viral RNA from challenge infection. Five μL of each RNA sample (equivalent to 1 μg RNA) was used for each RT-qPCR reaction. Results were reported as log 10 copy/μg of total RNA. For statistical purposes, samples that had undetected viral RNA level were assigned a value of 0 log RNA copy/1 μg of total RNA.

Results

Figure 4:
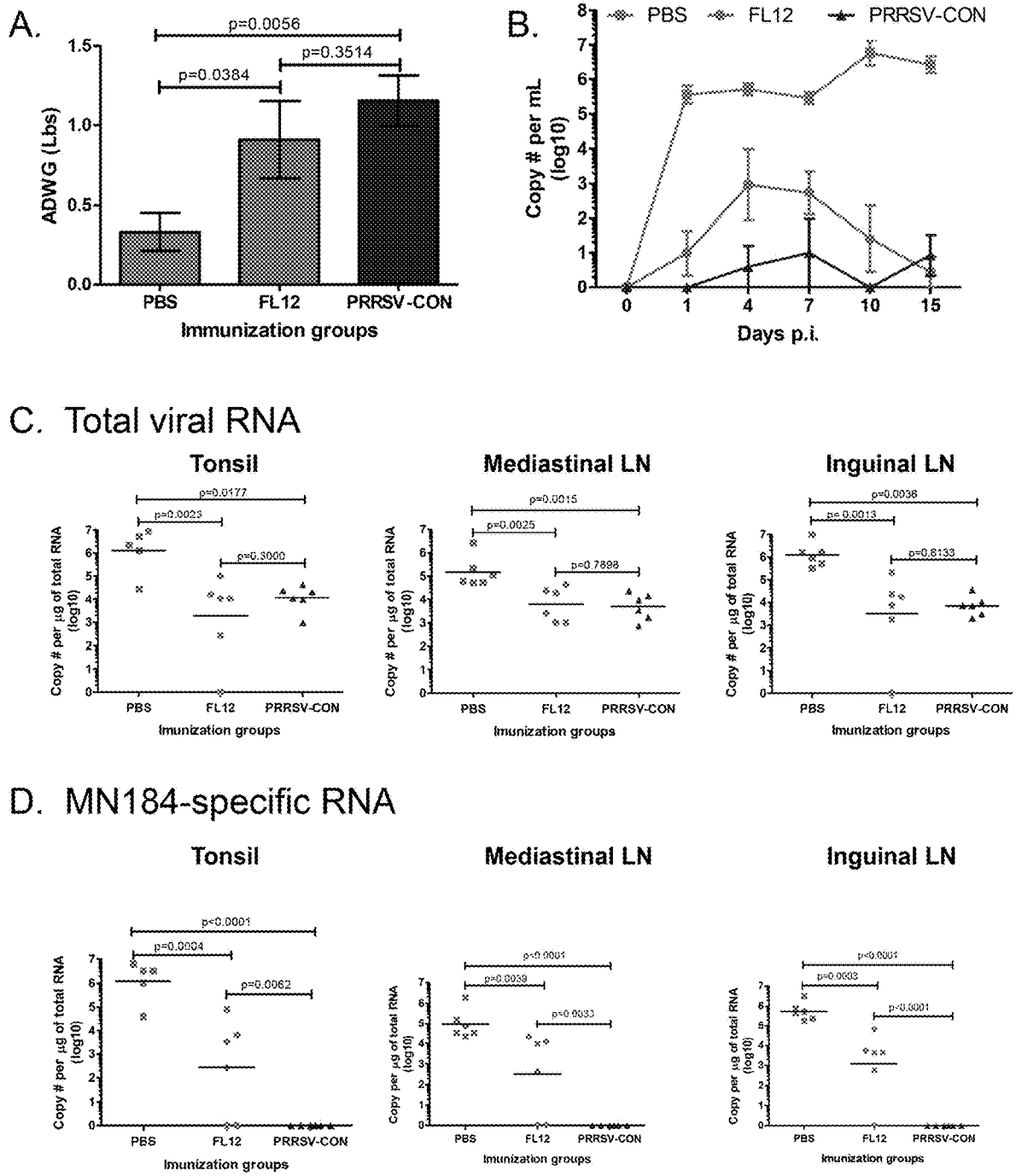
FIG. 4 is data demonstrating cross-protection provided by the PRRSV-CON described herein against the PRRSV-strain, MN-184. Panel (A) shows the average daily weight gain (ADWG) within 15 days after challenge-infection. Panel (B) shows the viremia levels after challenge determined by a commercial, universal RT-qPCR (Tetracore Inc., Rockville, Md.). Panel (C) shows total viral RNA levels in different tissues collected at 15 days post-challenge as determined by a commercial, universal RT-qPCR (Tetracore Inc., Rockville, Md.). Panel (D) shows the MN-184-specific RNA levels as determined by a differential RT-qPCR developed in-house.

The results of growth performance are presented in FIG. 4A. The mean ADWG of PBS-, PRRSV-CON- and FL12-immunized groups were 0.3 lbs (SD+/−0.3), 0.9 lbs (SD+/−0.6), and 1.2 lbs (SD+/−0.4), respectively. PRRSV-CON and FL12-immunized groups had greater ADWG than the PBS-immunized group. There was no statistical difference between the PRRSV-CON- and FL12-immunized groups.

The viremia levels after challenge infection are shown in FIG. 4B and Table 2. All pigs in the PBS-immunized group were viremic at all timepoints tested. The PRRSV-CON-immunized group only had 3 viremic pigs, of which 1 pig was viremic at 2 timepoints (pig #494 at 4 DPC and 7 DPC) and 2 pigs were viremic at only one timepoint (pigs #394 and 495 at 15 DPC). The remaining 3 pigs in this group (pigs #345, 410 and 459) were not viremic after challenge infection. By contrast, viremia was detected in 5 out of 6 pigs in the FL12-immunized group at two time-points or more after challenge infection. There was only 1 pig in this group (pig #440) that was not viremic at any time-point tested. Overall, the viremia level of PRRSV-CON-immunized pigs was significantly lower than that in the FL12-immunized group ($p<0.05$) and the PBS-immunized group ($p<0.0001$).

The results of total viral RNA quanititated by the universal RT-qPCR kit are shown in FIG. 4C. The PRRSV-CON- and FL12-immunized groups contained significantly lower levels of total viral RNA than the PBS-immunized group, regardless of the tissue types tested. However, there was no difference between the PRRSV-CON- and FL12-immunized groups in term of total viral RNA.

The results of MN-184 specific RNA quantitated by the differential RT-qPCR are shown in FIG. 4D. All pigs in PBS-immunized group carried MN-184 RNA in their tissues. Four pigs in the FL12-immunized group had MN-184 RNA in their tonsil and mediastinal lymph node, whereas 5 pigs in this group had MN-184 RNA in their inguinal lymph node. Remarkably, none of the pigs in the PRRSV-CON-immunized group had detectable level of MN-184 RNA in any of the tissue samples tested.

Taken together, these results clearly demonstrate that immunization of weaning pigs by infection with the non-naturally occurring PRRSV-CON resulted in significantly better cross-protection against challenge with PRRSV strain, MN-184, than did immunization with the PRRSV strain, FL12.

TABLE 2

Viremia After Challenge Infection (log10 copy/mL)

| Treatment | Pig ID | Day post-challenge infection (DPC) | | | | | |
|---|---|---|---|---|---|---|---|
| | | 0 DPC | 1 DPC | 4 DPC | 7 DPC | 10 DPC | 15 DPC |
| Group 1 | 365 | 0.00 | 4.94 | 5.43 | 5.45 | 6.79 | 6.32 |
| (Injected | 389 | 0.00 | 6.26 | 6.08 | 5.40 | 7.60 | 6.93 |
| ("immunized") | 407 | 0.00 | 4.91 | 6.00 | 5.86 | 7.56 | 6.75 |
| with PBS) | 416 | 0.00 | 6.20 | 6.04 | 5.20 | 7.18 | 6.78 |
| | 417 | 0.00 | 5.18 | 5.59 | 4.86 | 5.90 | 6.45 |
| | 435 | 0.00 | 5.83 | 5.08 | 5.94 | 5.57 | 5.36 |
| | Mean | 0.00 | 5.55 | 5.70 | 5.45 | 6.77 | 6.43 |
| | SD | 0.00 | 0.62 | 0.40 | 0.40 | 0.86 | 0.57 |

TABLE 2-continued

Viremia After Challenge Infection (log10 copy/mL)

| Treatment | Pig ID | 0 DPC | 1 DPC | 4 DPC | 7 DPC | 10 DPC | 15 DPC |
|---|---|---|---|---|---|---|---|
| Group 2 | 345 | 0.00 | 0.00 | 0.00 | 0.00 | 0.00 | 0.00 |
| (Immunized by | 394 | 0.00 | 0.00 | 0.00 | 0.00 | 0.00 | 2.58 |
| infection with | 410 | 0.00 | 0.00 | 0.00 | 0.00 | 0.00 | 0.00 |
| PRRSV-CON) | 459 | 0.00 | 0.00 | 0.00 | 0.00 | 0.00 | 0.00 |
|  | 494 | 0.00 | 0.00 | 3.58 | 5.98 | 0.00 | 0.00 |
|  | 495 | 0.00 | 0.00 | 0.00 | 0.00 | 0.00 | 2.98 |
|  | Mean | 0.00 | 0.00 | 0.60 | 1.00 | 0.00 | 0.93 |
|  | SD | 0.00 | 0.00 | 1.46 | 2.44 | 0.00 | 1.44 |
| Group 3 | 349 | 0.00 | 0.00 | 2.81 | 2.92 | 0.00 | 0.00 |
| (Immunized by | 381 | 0.00 | 0.00 | 0.00 | 3.04 | 2.86 | 0.00 |
| infection with | 440 | 0.00 | 0.00 | 0.00 | 0.00 | 0.00 | 0.00 |
| FL12) | 455 | 0.00 | 0.00 | 4.18 | 4.34 | 0.00 | 0.00 |
|  | 487 | 0.00 | 3.59 | 5.28 | 2.40 | 5.60 | 2.68 |
|  | 507 | 0.00 | 2.32 | 5.56 | 3.70 | 0.00 | 0.00 |
|  | Mean | 0.00 | 0.99 | 2.97 | 2.73 | 1.41 | 0.45 |
|  | SD | 0.00 | 1.58 | 2.50 | 1.50 | 2.35 | 1.09 |

Example 6—Evaluation of the Level of Cross-Protection Against PRRSV Strain 16244B Materials and Methods The experimental design was the same as described above in Example 5. A total of 18 PRRSV-seronegative, 3 week-old pigs purchased from the UNL research farm were randomly assigned into 3 experimental groups. Each group was housed in a separate room at the Biosecurity Level-2 Animal Research Facilities at UNL, following the regulations established by the Institutional Animal Care and Use Committee. Group 1 was injected with PBS and acted as the control. Group 2 was immunized, intramuscularly, by infection with PRRSV-CON at the dose of $10^{4.0}$ TCID$_{50}$ per pig. Group 3 was immunized, intramuscularly, by infection with the wild type PRRSV, FL12, at the dose of $10^{4.0}$ TCID$_{50}$ per pig. See Table 3. One pig in group 3 (pig #543) and one pig in group 2 (pig #435) were removed from this study on 14 and 23 days after primary infection, respectively, due to lameness in their legs. At day 52 post-infection (p.i.), all pigs were challenged, intramuscularly, with PRRSV strain 16244B at the challenge dose of $10^{5.0}$ TCID$_{50}$. Parameters used to evaluate protection by immunization with the PRRSV-CON virus, including viremia and viral load in various tissues as well as growth performance, were measured as described above in Example 5.

TABLE 3

Experimental Design to Evaluate Level of Cross-Protection Against PRRSV Strain 16244B

| Groups | Immunized with | Challenged with |
|---|---|---|
| 1 (n = 6) | PBS | 16244B |
| 2 (n = 6) | PRRSV-CON | (sub-group 3) |
| 3 (n = 6) | PRRSV strain FL12 |  |

Results

Figure 5:
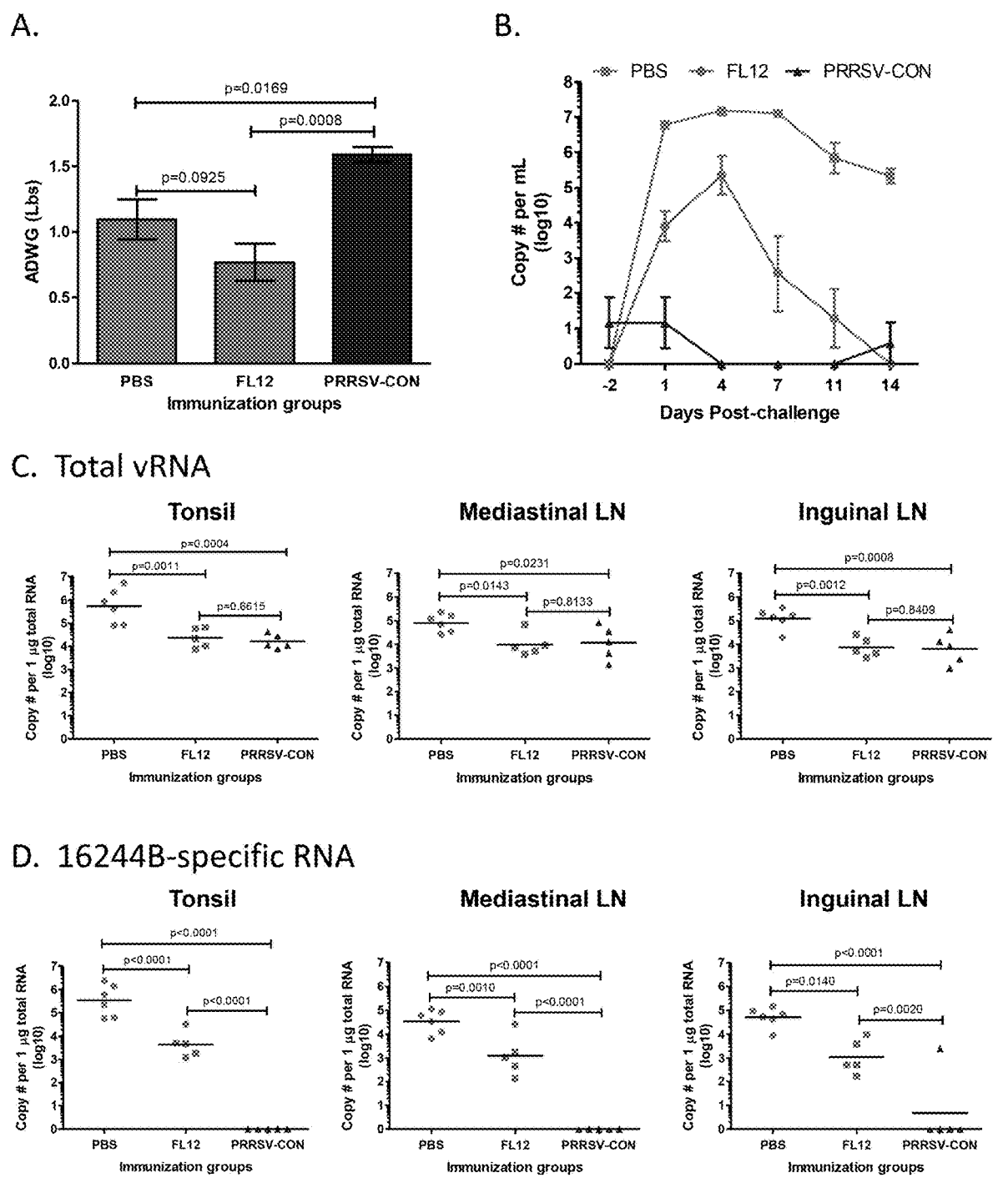

The results of growth performance are shown in FIG. 5A. Mean ADWG of PBS-, PRRSV-CON-, and FL12-immunized groups were 1.1 lbs (SD+/−0.3), 1.6 lbs (SD+/−0.1), and 0.8 lbs (SD+/−0.3), respectively. The PRRSV-CON-immunized group had greater ADWG than the PBS-immunized group and the FL12-immunized group; whereas the FL12-immunized group was not statistically different from the PBS-immunized group.

The results of viremia levels after challenge infection are shown in FIG. 5B and Table 4. All pigs in the PBS-immunized group were viremic at all timepoints tested. Two out of 5 pigs in the PRRSV-CON-immunized group (pigs #442 and 445) did not resolve viremia at 52 days after primary infection as viral RNA was still detected in their serum samples collected at this timepoint. After challenge infection, 3 pigs in the PRRSV-CON-immunized group were viremic at only 1 timepoint. The remaining 2 pigs in this group (pigs #436 and 438) were not viremic throughout the period of 15 days post-challenge. By contrast, all pigs in the FL12-immunized group resolved viremia by 52 days post-primary infection. After challenge infection, all pigs in this group became viremic. Overall, the viremia level of the PRRSV-CON-immunized group was significantly lower than that of the FL12-immunized group (p<0.0001) or the PBS-immunized group (p<0.0001).

The results of total viral RNA quantitated by the commercial RT-qPCR kit (Tetracore Inc., Rockville, Md.) are shown in FIG. 5C. Both the PRRSV-CON- and FL12-immunized groups contained significantly lower levels of total viral RNA than the PBS-immunized group, regardless of the tissue types tested. However, there was no statistical difference between the PRRSV-CON-immunized group and the FL12-immunized group in terms of total viral RNA.

The results of 16244B-specific RNA quantitated by the differential RT-qPCR are shown in FIG. 5D. All pigs in the PBS- and FL12-immunized groups carried 16244B-specific RNA in their tissues, although the levels of 16244B RNA in the FL12-immunized group was lower than those in the PBS-immunized group. By contrast, only 1 pig in the PRRSV-CON-immunized group carried 16244B-specific RNA in its inguinal lymph node, while the remaining 4 pigs in this group did not carry 16244B-specific RNA.

All together, these results clearly demonstrate that immunization of weaning pigs by infection with the non-naturally occurring PRRSV-CON resulted in significantly better cross-protection against challenge with PRRSV strain, 16244B, than did immunization with the PRRSV strain, FL12.

TABLE 4

Level of Viremia After Challenge Infection (log10 copy/mL)

| Treatment | Pig ID | 0 DPC | 1 DPC | 4 DPC | 7 DPC | 11 DPC | 14 DPC |
|---|---|---|---|---|---|---|---|
| Group 1 (Injected with PBS) | 440 | 0.00 | 6.62 | 6.99 | 6.79 | 6.15 | 4.67 |
| | 441 | 0.00 | 6.61 | 6.93 | 7.11 | 5.79 | 4.81 |
| | 544 | 0.00 | 6.85 | 6.82 | 6.96 | 3.91 | 5.68 |
| | 545 | 0.00 | 7.11 | 7.41 | 7.11 | 6.81 | 5.93 |
| | 546 | 0.00 | 6.74 | 7.45 | 7.30 | 5.67 | 5.40 |
| | 547 | 0.00 | 6.77 | 7.51 | 7.36 | 6.73 | 5.52 |
| | Mean | 0.00 | 6.78 | 7.18 | 7.11 | 5.84 | 5.34 |
| | SD | 0.00 | 0.18 | 0.30 | 0.21 | 1.06 | 0.50 |
| Group 2 (immunized by infection with PRRSV-CON) | 435 | Removed from experiment on day 23rd after primary infection | | | | | |
| | 436 | 0.00 | 0.00 | 0.00 | 0.00 | 0.00 | 0.00 |
| | 437 | 0.00 | 2.48 | 0.00 | 0.00 | 0.00 | 0.00 |
| | 438 | 0.00 | 0.00 | 0.00 | 0.00 | 0.00 | 0.00 |
| | 442 | 2.81 | 0.00 | 0.00 | 0.00 | 0.00 | 2.93 |
| | 445 | 3.00 | 3.32 | 0.00 | 0.00 | 0.00 | 0.00 |
| | Mean | 1.16 | 1.16 | 0.00 | 0.00 | 0.00 | 0.59 |
| | SD | 1.59 | 1.62 | 0.00 | 0.00 | 0.00 | 1.31 |
| Group 3 (immunized by infection with FL12) | 439 | 0.00 | 4.34 | 6.78 | 3.54 | 2.48 | 0.00 |
| | 444 | 0.00 | 3.04 | 6.58 | 0.00 | 0.00 | 0.00 |
| | 446 | 0.00 | 5.26 | 4.84 | 0.00 | 0.00 | 0.00 |
| | 526 | 0.00 | 2.98 | 4.40 | 4.15 | 0.00 | 0.00 |
| | 540 | 0.00 | 3.90 | 4.18 | 5.08 | 3.95 | 0.00 |
| | 543 | Removed from experiment on day 14th after primary infection | | | | | |
| | Mean | 0.00 | 3.90 | 5.35 | 2.55 | 1.29 | 0.00 |
| | SD | 0.00 | 0.95 | 1.23 | 2.39 | 1.84 | 0.00 |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A non-structural PRRSV-CON polypeptide having a sequence selected from the group consisting of SEQ ID NO:3, 5, and 7.

2. The polypeptide of claim 1, wherein the polypeptide is encoded by a nucleic acid, respectively, having a sequence selected from the group consisting of SEQ ID NO:2, 4, and 6.

3. A virus particle comprising the non-structural PPRSV-CON polypeptide of claim 1.

4. A composition comprising the virus particle of claim 3 and a pharmaceutically acceptable carrier.

5. The composition of claim 4, further comprising an adjuvant.

6. A composition comprising the non-structural polypeptide of claim 1 and a pharmaceutically acceptable carrier.

7. The composition of claim 6, further comprising an adjuvant.

8. A method for eliciting an immune response to PPRSV in a porcine, comprising administering, to a porcine:
   (i) an effective amount of the polypeptide of claim 1;
   (ii) an effective amount of the virus particle of claim 3; or
   (iii) an effective amount of the composition of claim 6.

9. The method of claim 8, wherein the administration is selected from the group consisting of intramuscularly, intraperitoneally, and orally.

10. A method for treating or preventing PPRS in a porcine, comprising administering, to a porcine:
    (i) an effective amount of the polypeptide of claim 1;
    (ii) an effective amount of the virus particle of claim 3; or
    (iii) an effective amount of the composition of claim 6.

11. The method of claim 10, wherein the administration is selected from the group consisting of intramuscularly, intraperitoneally, and orally.

* * * * *

SEQUENCE LISTING

```
<160> NUMBER OF SEQ ID NOS: 43

<210> SEQ ID NO 1
<211> LENGTH: 15456
<212> TYPE: DNA
<213> ORGANISM: Porcine reproductive and respiratory syndrome virus

<400> SEQUENCE: 1
atgacgtata ggtgttggct ctatgccatg acatttgtat tgtcaggagc tgcgaccatt      60
ggtacagccc aaaactagct gcacagaaaa cgcccttctg tgacagccct cttcagggga     120
gcttaggggt ctgtccctag caccttgctt ccggagttgc actgctttac ggtctctcca     180 acccttaac catgtctggg atacttgatc ggtgcacgtg tacccccaat gccagggtgt      240
ttatggcgga gggccaagtc tactgcacac gatgtctcag tgcacggtct ctccttcctc     300
tgaatctcca agttcctgag ctcggggtgc tgggcctatt tacaggccc gaagagccac      360 tccggtggac gttgccacgt gcattcccca ctgtcgagtg ctcccccgcc ggggcctgct     420
ggctttctgc gatctttcca attgcacgaa tgaccagtgg aaacctgaac tttcaacaaa     480
```

```
gaatggtgcg ggtcgcagct gagctttaca gagccggcca gctcacccct gcagtcttga    540
aggctctaca agtttatgaa cggggttgcc gctggtaccc cattgttgga cctgtccctg    600
gagtggccgt tttcgccaac tccctacatg tgagtgataa acctttcccg ggagcaactc    660
atgtgttaac caacctgccg ctcccgcaga ggcccaagcc tgaagacttt tgccccttig    720 agtgtgctat ggctgacgtc tatgacattg tcatgacgc cgtcatgtat gtggccgaag    780
ggaaagtctc ctgggcccct cgtggcgggg atgaagggaa atttgaaact gtccccgagg    840
agttgaagtt gattgcgaac cgactccaca tctccttccc gccccaccac gcagtggaca    900
tgtctaagtt tgccttcata gcccctggga gtggtgtttc catgcgggtc gagtgccaac    960
acggctgcct ccccgctgac actgtccctg aaggcaactg ctggtggcgc ttgtttgact   1020
tgctcccact ggaagttcag aacaaagaaa ttcgccatgc taaccaattt ggctatcaga   1080
ccaagcatgg tgtcgctggc aagtacctac agcggaggct gcaagttaat ggtctccgag   1140
cagtgactga cccaaatgga cctatcgtcg tacagtattt ctctgttaag gagagctgga   1200
tccgccactt aagactggcg gaagaaccta gcctccctgg gtttgaggac ctcctcagaa   1260
taagggttga gcccaacacg tcgccattgg ctgacaagga tgagaaaatc ttccggtttg   1320
gcagtcacaa gtggtacggt gctggaaaga gggcaaggaa agcacgctct ggtgcgactg   1380
ccacagtcgc tcaccgcgct ttgcccgctc gtgaaaccca gcaggccaag aagcacgagg   1440
ttgccagcgc caacaaggct gagcatctca agcactattc cccgcctgcc gacgggaact   1500
gtggttggca ctgcatttcc gccatcgcca accggatggt gaattccaaa tttgaaacca   1560
cccttcccga aagagtgaga ccttcagatg actgggctac tgacgaggat cttgtgaata   1620
ccatccaaat cctcaggctc cctgcggcct tggacaggaa cggtgcttgt gctagcgcca   1680
agtacgtgct taagctggaa ggtgagcatt ggactgtctc tgtgaccccct gggatgtccc   1740 cttctttgct ccccctigaa tgtgttcagg gctgttgtga gcataagggc ggtcttggtt   1800
ccccagatgc ggtcgaagtt tccggatttg accctgcctg ccttgaccga ctggctgagg   1860
tgatgcactt gcctagcagt gccatcccag ccgctctggc cgaaatgtcc ggcgacccca   1920
atcgtccggc ttccccggtc accactgtgt ggactgtttc gcagttcttt gcccgtcaca   1980
gaggaggaga gcaccctgat caggtgtgct tagggaaaat catcagcctt tgtcaggtga   2040
ttgaggaatg ctgctgttcc cagaacaaaa ccaaccgggt caccccggaa gaggtcgcgg   2100
caaagattga ccagtacctc cgtggtgcaa caagtcttga agaatgcttg ccaggcttg    2160 agagggctcg cccgccgagc gcaatggaca cctcctttga ttggaatgtt gtgctccctg   2220
gggttgaggc ggcaactcag acaaccaaac agccccatgt caaccagtgc cgcgctctgg   2280
tccctgtcgt gactcaagag tctttggaca aagactcggt ccctctgacc gccttctcgc   2340
tgtctaattg ctactaccct gcacaaggtg acgaggttcg tcaccgtgag aggctaaact   2400
ccgtgctctc taagttggag gaggttgttc gtgaggaata tggctcacg ccaactggac    2460 ctggcccgcg acccgcactg ccgaacgggc tcgacgaact aaagaccag atggaggagg    2520 atctgctgaa actagtcaac gcccaggcaa cttcagaaat gatggcctgg gcagccgagc   2580
aggttgatct aaaagcttgg gtcaaaaact acccacggtg gacaccgcca ccccctccac   2640
caagagttca gcctcgaaaa acgaagtctg tcaagagctt gccagagaac aagcctgtcc   2700
ctgctccgcg caggaaggtc agatctgatt gtggcagccc gattttaatg ggcgacaatg   2760
tccctaacag ttgggaagat ttggctgttg gtggcccccct tgatctctcg acaccacccg   2820
```

```
agccgatgac acctctgagt gagcctgcac ttatgcccgc gttgcaacat atttctaggc    2880
cagtgacacc tttgagtgtg ccggcccaa ttcctgcacc gcgcagagct gtgtcccgac     2940
cggtgacgcc ctcgagtgag ccaatttctg tgtctgcacc gcgacataaa tttcagcagg    3000
tggaagaagc gaatctggcg gcagcaacgc tgacgtacca ggacgaaccc ctagatttgt    3060
ctgcatcctc acagactgaa tatgaggctt ctcccctagc accactgcag aacatgggta    3120
ttctggaggt gggggggcaa gaagctgagg aaattctgag tgaaatctcg gacataccga    3180
atgacatcaa ccctgcgcct gtgtcatcaa gcagctccct gtcaagcgtt aagatcacac    3240
gcccaaaata ctcagctcaa gccatcatcg actcgggcgg ccctgcagt gggcatctcc     3300 aaaaggaaaa agaagcatgc ctcagcatca tgcgtgaggc ttgtgatgcg actaagcttg    3360
gtgaccctgc cacgcaggaa tggctttctc gcatgtggga tagggtggac atgctgactt    3420
ggcgcaacac gtctgcttac caggcgtttc gcaccttaga tggcaggttt gagtttctcc    3480
caaagatgat actcgagaca ccgccgcccct cccgtgtgg gttgtgatg ctgcctcaca     3540 cgcctgcacc ttccgtgggt gcggagagcg accttaccat tggttcagtc gccactgaag    3600
atgttccacg catcctcggg aaaatagaaa atgccggcga gatgaccaac cagggaccct    3660
tggcatcctc cgaggaagaa ccggcagacg accaacctgc caaagactcc cggatatcgt    3720 cgcggggtt tgacgagagc acagcagctc cgtccgcagg cacaggtggc gccggcttat    3780
ttactgattt gccaccttca gacggtgtag atgcggacgg ggggggccg ttacagacgg     3840 taaaaagaa agctgaaagg ctcttcgacc aattgagccg tcaggttttt aacctcgtct     3900
cccatctccc tgttttcttc tcacacctct tcaaatctga cagtggttat tctccgggtg    3960
attggggttt tgcagctttt actctatttt gcctcttttt atgttacagt tacccattct    4020
ttggttttgc tcccctcttg ggtgtgtttt ctgggtcttc tcggcgcgtg cgcatggggg    4080
tttttggctg ctggttggct tttgctgttg gtctgttcaa gcctgtgtcc gacccagtcg    4140
gcactgcttg tgagtttgat cgccagagt gtaggaacgt ccttcattct tttgagcttc     4200
tcaaaccttg ggaccctgtt cgcagccttg ttgtgggccc cgtcggtctc ggtcttgcca    4260
ttcttggcag gttactgggc ggggcacgct acatctggca ttttttgctt aggcttggca    4320
ttgttgcaga ctgtatcttg gctggagctt atgtgctttc tcaaggtagg tgtaaaaagt    4380 gctgggatc ttgtataaga actgctccta atgagatcgc cttaacgtg ttcccttttta     4440 cacgtgcgac caggtcgtca ctcatcgacc tgtgcgatcg gttttgtgcg ccaaaaggca    4500
tggaccccat tttcctcgcc actgggtggc gcgggtgctg gaccggccga agccccattg    4560 agcaacctc tgaaaaaccc atcgcgtttg cccagttgga tgaaaagaag attacggcta     4620
ggactgtggt cgcccagcct tatgacccca accaagccgt aaagtgcttg cgggtgttac    4680
aggcgggtgg ggcgatggtg gctgaggcag tcccaaaagt ggtcaaggtt ccgctattc     4740 cattccgagc cccctttttt cccaccggag tgaaagttga ccctgagtgc aggatcgtgg    4800
ttgaccccga cactttcact acagctctcc ggtctggcta ctccaccaca aacctcgtcc    4860
ttggtgtggg ggactttgcc cagctgaatg gattaaaaat caggcaaatt tccaagcctt    4920
caggaggagg cccacacctc attgctgccc tgcatgttgc ctgctcgatg gcgttgcaca    4980
tgcttgctgg gatttatgta actgcagtgg ggtcttgcgg taccggcacc aacgatccgt    5040
ggtgcactaa cccgtttgcc gtccctggct acggacctgg ctctctctgc acgtccagat    5100
tgtgcatctc ccaacatggc cttaccctgc ccttgacagc acttgtggca ggattcggtc    5160
ttcaggaaat tgccttggtt gttttgattt tcgtttccat cggaggcatg gctcacaggt    5220
```

```
tgagttgcaa ggctgatatg ctgtgcgttt tacttgcaat cgccagctat gtttgggtac    5280
cccttacctg gttgctttgt gtgtttcctt gctggttgcg ctggttctct ttgcaccccc    5340
tcaccatcct atggttggtg tttttcttga tttctgtaaa tatgccttca ggaatcttgg    5400
ccgtggtgtt gttggtttct ctttggcttc taggtcgtta tactaatgtt gctggtcttg    5460
tcacccccta tgacattcat cattacacca gtggcccccg cggtgttgcc gccttggcta    5520
ccgcaccaga tgggacctac ttggccgctg tccgccgcgc tgcgttgact ggccgcacca    5580
tgctgtttac cccgtctcag cttgggtccc ttcttgaggg tgctttcaga actcaaaagc    5640
cctcactgaa caccgtcaat gtggtcgggt cctccatggg ctctggcggg tgttcacca    5700 tcgacgggaa aattaagtgc gtaactgccg cacatgtcct tacgggtaat tcagctaggg    5760
tttccggggt cggcttcaat caaatgcttg actttgatgt aaaaggggac ttcgccatag    5820
ctgattgccc gaattggcaa ggggctgctc ccaagaccca attctgcaag gatggatgga    5880
ctggccgtgc ctattggctg acatcctctg gcgtcgaacc cggtgtcatt gggaatggat    5940
tcgccttctg cttcaccgcg tgcggcgatt ccgggtcccc agtgatcacc gaagccggtg    6000
agcttgtcgg cgttcacaca ggatcaaaca aacaaggagg aggcattgtc acgcgcccct    6060
caggccagtt ttgtaatgtg gcacccatca agctgagcga attaagtgaa ttctttgctg    6120
gacctaaggt cccgctcggt gatgtgaagg ttggcagcca cataattaaa gacataagcg    6180
aggtgccttc agatctttgc gccttgcttg ctgccaaacc cgaactggaa ggaggcctct    6240
ccaccgtcca acttctgtgt gtgttttttcc tcctgtggag aatgatggga catgcctgga    6300
cgcccttggt tgctgtgggt tttttatct tgaatgaggt tctcccagct gtcctggtcc    6360
ggagtgtttt ctcctttgga atgtttgtgc tatcttggct cacaccatgg tctgcgcaag    6420
ttctgatgat caggcttcta acagcagctc ttaacaggaa cagatggtca cttgccttt    6480 acagcctcgg tgcagtgacc ggttttgtcg cagatcttgc ggcaactcag gggcatccgt    6540
tgcaggcagt gatgaattta agcacctatg ccttcctgcc tcggatgatg gttgtgacct    6600
caccagtccc agtgattgcg tgtggtgttg tgcacctcct tgccataatt ttgtacttgt    6660
ttaagtaccg ttgcctgcac aatgtccttg ttggcgatgg agtgttctct gcggcttttct   6720 tcttgcgata ctttgccgag ggaaagttga gggaagggt gtcgcaatcc tgcgggatga    6780
atcatgagtc actgactggt gccctcgcta tgagactcaa tgacgaggac ttggatttcc    6840
ttacgaaatg gactgatttt aagtgctttg tttctgcgtc caacatgagg aatgcagcgg    6900
gccaattcat cgaggctgcc tatgctaaag cacttagagt agaacttgcc cagttggtgc    6960
aggttgataa ggttcgaggt actttggcca aacttgaagc ttttgctgat accgtggcac    7020
cccaactctc gcccggtgac attgttgttg ctcttggcca cacgcctgtt ggcagtatct    7080
tcgacctaaa ggttggtagc accaagcata ccctccaagc cattgagacc agagtccttg    7140
ccgggtccaa aatgaccgtg gcgcgcgtcg ttgacccaac ccccacgccc caccccgcac    7200
ccgtgcccat ccccctccca ccgaaagttc tggagaatgg ccccaacgcc tgggggatg    7260 aggaccgttt gaataagaag aagaggcgca ggatggaagc cgtcggcatc tttgttatgg    7320
gcgggaagaa gtaccagaaa ttttgggaca agaattccgg tgatgtgttt tatgaggagg    7380
tccatgataa cacagatgcg tgggagtgcc tcagagttgg cgaccctgcc gactttgacc    7440
ctgagaaggg aactctgtgt gggcatacca ccattgaaga taaggcttac aatgtctacg    7500
cctccccatc tggcaagaag ttcctggtcc ccgtcaaccc agagagcgga agagcccaat    7560
```

```
gggaagctgc aaagctttcc gtggagcagg cccttggcat gatgaatgtc gacggtgaac    7620
tgacagccaa agaactggag aaactgaaaa gaataattga caaactccag ggcctgacta    7680
aggagcagtg tttaaactgc tagccgccag cggcttgacc cgctgtggtc gcggcggctt    7740
ggttgttact gagacagcgg taaaaatagt caaatttcac aaccggacct tcaccctagg    7800
acctgtgaat ttaaaagtgg ccagtgaggt tgagctaaaa gacgcggtcg agcacaacca    7860
acacccggtt gcaagaccgg ttgatggtgg tgttgtgctc ctgcgctccg cagttccttc    7920
gcttatagac gtcttgatct ccggtgctga tgcatctccc aagttactcg cccgccacgg    7980
gccgggaaac actgggatcg atggcacgct ttgggatttt gaggccgaag ccaccaaaga    8040
ggaaatcgca ctcagtgcgc aaataataca ggcttgtgac attaggcgcg cgacgcacc    8100 tgaaattggt ctcccttaca agctgtaccc tgttaggggc aaccctgagc gggtaaaagg    8160
agttttgcag aatacaaggt ttggagacat accttacaaa accccagtg acactggaag    8220 cccagtgcac gcggctgcct gcctcacgcc caatgccact ccggtgactg atgggcgctc    8280
cgtcttggcc acgaccatgc cctccggttt tgagttgtat gtaccgacca ttccagcgtc    8340
tgtccttgat tatcttgatt ctaggcctga ctgccccaaa cagttgacag agcacggctg    8400
tgaggatgcc gcattgagag acctctccaa gtatgacttg tccacccaag ctttgttttt    8460
gcctggagtt cttcgccttg tgcgtaagta cctgtttgcc catgtgggta agtgcccgcc    8520
cgttcatcgg ccttccactt accctgccaa gaattctatg gctggaataa atgggaacag    8580
gtttccaacc aaggacattc agagcgtccc tgaaatcgac gttctgtgcg cacaggccgt    8640
gcgagaaaac tggcaaactg ttaccccttg taccctcaag aaacagtatt gcgggaagaa    8700
gaagactagg acaatactcg gcaccaataa cttcattgcg ctggcccacc gggcagcgtt    8760
gagtggtgtc acccagggct tcatgaaaaa ggcgtttaac tcgcccatcg ccctcgggaa    8820
aaacaaattt aaggagctac agactccggt cttgggcagg tgccttgaag ctgatcttgc    8880
atcctgcgat cgatccacac ctgcaattgt ccgctggttt gccgccaatc ttctttatga    8940
acttgcctgt gctgaagagc atctaccgtc gtacgtgctg aactgctgcc acgacttact    9000
ggtcacgcag tccggcgcag tgactaagag aggtggcctg tcgtctggcg acccgatcac    9060
ttctgtgtcc aacaccattt acagcttggt gatatatgca cagcacatgg tgctcagtta    9120
ctttaaaagt ggtcacccc atggccttct gtttctacaa gaccagctaa agtttgagga    9180
catgctcaag gttcaacccc tgatcgtcta ttcggacgac ctcgtgctgt atgccgagtc    9240
tcccaccatg ccaaactacc actggtgggt tgaacatctg aacctgatgc tgggttttca    9300
gacggaccca agaagacag ccataacaga ctcgccatca tttctaggct gtaggataat    9360
aaatgggcgc cagctagtcc ccaaccgtga caggattctc gcggccctcg cctaccacat    9420
gaaggcgagc aatgtttctg aatactacgc ctcggcggct gcaatactca tggacagctg    9480
tgcttgtttg gagtatgatc ctgaatggtt tgaagaactt gtggttggaa tagcgcagtg    9540
cgcccgcaag gacggctaca gctttccgg cccgccgttc ttcttgtcca tgtgggaaaa    9600
actcaggtcc aattatgagg ggaagaagtc cagagtgtgc gggtactgcg ggccccggc    9660 cccgtacgcc actgcctgtg gcctcgacgt ctgtatttac cacacccact tccaccagca    9720
ttgtccagtc ataatctggt gtggccatcc agcgggttct ggttcttgta gtgagtgcaa    9780 accccccta gggaaaggca caagccctct agatgaggtg ttggaacaag tcccgtataa    9840
gcctccacgg accgtaatca tgcatgtgga gcagggtctc acctctcttg acccaggcag    9900
ataccagact cgccgcggat tagtctccgt taggcgtggc atcaggggaa atgaagttga    9960
```

```
cctaccagac ggtgattatg ctagcaccgc cttgctcccc acttgtaaag agatcaacat    10020
ggtcgctgtc gcttctaatg tgttgcgcag caggttcatc atcggtccac ccggtgctgg    10080
gaaaacatac tggctccttc aacaggtcca ggatggtgat gtcatttaca caccaactca    10140
tcagaccatg cttgacatga ttaaggcttt ggggacgtgc cggttcaacg tcccggcagg    10200
cacaacgctg caattccctg cccccctcccg taccggcccg tgggttcgca tcctggccgg    10260
cggttggtgt cctggcaaga attccttcct ggatgaagca gcgtattgta atcaccttga    10320
tgtcttgagg cttcttagca aaactaccct cacctgtctg ggagacttca acaactcca    10380 cccagtgggt tttgattctc attgctatgt ttttgacatc atgcctcaga ctcaactgaa    10440
gaccatctgg aggtttggac agaatatctg tgatgccatt cagccagatt acagggacaa    10500
acttgtgtcc atggtcaaca caacccgtgt aacctacgtg gaaaaacctg tcaagtatgg    10560
gcaagtcctc accccttacc acagggaccg agaggacggc gccatcacaa ttgactccag    10620
tcaaggcgcc acatttgatg tggttacatt gcatttgccc actaaagatt cactcaacag    10680
gcaaagagcc cttgttgcta tcaccagggc aagacatgct atctttgtgt atgacccaca    10740
caggcaactg cagagcatgt ttgatcttcc tgcaaaaggc acacccgtca acctcgccgt    10800
gcaccgtgac gagcagctga tcgtgctaga tagaaataac aaagaatgca cggttgctca    10860
ggctctaggc aatggggata aattcagggc cacagacaag cgcgttgtag attctctccg    10920
cgccatttgt gcagatctag aagggtcgag ctctccgctc cccaaggtcg cacacaactt    10980
gggattttat ttctcacctg atttgacaca gtttgctaaa ctcccggtag aacttgcacc    11040
ccactggccc gtggtgacaa cccagaacaa tgaaaagtgg ccagaccggc tggttgccag    11100
ccttcgccct atccataaat atagccgcgc gtgcatcggt gccggctata tggtgggccc    11160
ctcggtgttt ctaggcaccc ctgggttgt gtcatactat ctcacaaaat ttgttaaggg    11220
cgaggctcaa gtgcttccgg agacagtctt cagcaccggc cgaattgagg tagattgccg    11280
ggagtatctt gatgatcggg agcgagaagt tgctgagtcc ctcccacatg ccttcattgg    11340
cgacgtcaaa ggcactaccg ttggaggatg tcaccatgtc acctccaaat accttccgcg    11400
cttccttccc aaggaatcag ttgcggtagt cggggtttca agccccggga aagccgcaaa    11460
agcagtttgc acattaacag atgtgtacct cccagacctt gaagcttacc tccacccaga    11520
gacccagtcc aagtgctgga aaatgatgtt ggacttcaag gaagttcgac tgatggtctg    11580
gaaagacaaa acggcctatt ttcaacttga aggccgccat ttcacctggt atcagcttgc    11640
aagctatgcc tcgtacatcc gagttcctgt taactctacg gtgtatttgg accccctgcat    11700 gggccctgcc ctttgcaaca gaagagttgt cgggtccact cattgggggg ctgacctcgc    11760
agtcaccccc tatgattatg gtgccaaaat cattctgtct agtgcatacc atggtgaaat    11820
gcctcctggg tacaaaatcc tggcgtgcgc ggagttctcg cttgacgatc cagtgaggta    11880
caaacacacc tggggggttg aatcggatac agcgtatctg tacagttca ccggaaacgg    11940 tgaggactgg gaggattaca atgatgcgtt tcgtgcgcgc cagaaaggga aaatttataa    12000
ggccactgcc accagcatga ggtttcattt tccccccgggc cctgtcattg aaccaacttt    12060
gggcctgaat tgaaatgaaa tggggggctat gcaaagcctt tttgacaaaa ttggccaact    12120
ttttgtggat gctttcacgg aatttttggt gtccattgtt gatatcatca tatttttggc    12180
cattttgttt ggcttcacca tcgccggttg gctggtggtc ttttgcatca gattgggtttg    12240 ctccgcggta ctccgtgcgc gccctaccat tcaccctgag caattacaga agatcctatg    12300
```

```
aggcctttct ttctcagtgc cgggtggaca ttcccacctg gggaactaaa catcccttgg   12360
ggatgctttg gcaccataag gtgtcaaccc tgattgatga aatggtgtcg cgtcgaatgt   12420
accgcatcat ggaaaaagca ggacaggctg cctggaaaca ggtggtgagc gaggctacgc   12480
tgtctcgcat tagtggtttg gatgtggtgg ctcattttca gcatcttgcc gccattgaag   12540
ccgagacctg taaatatttg gcctctcggc tgcccatgct acacaacctg cgcatgacag   12600
ggtcaaatgt aaccatagtg tataatagta ctttgaatca ggtgtttgct atttttccaa   12660
cccctggttc ccggccaaag cttcatgatt ttcagcaatg gctaatagct gtgcattcct   12720
ccatattttc ctctgttgca gcttcttgta ctcttttgt tgtgctgtgg ttgcggattc   12780
caatgctacg tactgttttt ggtttccact ggttaggggc aattttttcct tcgaactcac   12840 agtgaattac acggtgtgtc caccttgcct cacccggcaa gcagccgctg agatctacga   12900
acccggcagg tctcttttggt gcaggatagg gcatgaccga tgtagggagg acgatcatga   12960
cgaactaggg ttcatggttc cgcctggcct ctccagcgaa ggccacttga ccagtgttta   13020
cgcctggttg gcgttcctgt ccttcagcta cacggcccag ttccatcccg agatatttgg   13080
gatagggaat gtgagtcaag tttatgttga catcaagcac caattcatct gcgccgaaca   13140
tgacgggcag aacgccacct tgcctcgcca tgacaacatt tcagccgtgt ttcagaccta   13200
ctaccaacat caggtcgacg gcggcaattg gtttcaccta gaatggctgc gcccccttctt   13260 ttcctcttgg ttggttttaa atgtttcgtg gtttctcagg cgttcgcctg caagccatgt   13320
ttcagttcga gtctttcaga catcaagacc aacaccaccg cagcagcaag ctttgttgtc   13380
ctccaagaca tcagctgcct taggcatggc gactcgtcct ctgaggcgat cgcaaaagc   13440 tctcagtgcc gcacggcgat agggacaccc gtgtacatca ccatcacagc caatgtgaca   13500
gatgagaatt atttacattc ttctgatctc ctcatgcttt cttcttgcct tttctatgct   13560
tctgagatga gtgaaaaggg attcaaggtg gtatttggca atgtgtcagg catcgtggct   13620
gtgtgtgtca actttaccag ctacgtccaa catgtcaagg agtttaccca acgctccttg   13680
gtggtcgacc atgtgcggct gcttcatttc atgacacctg agaccatgag gtgggcaacc   13740
gttttagcct gtctttttgc cattctgttg gcaatttgaa tgttcaagta tgttggggaa   13800
atgcttgacc gcgggctgtt gctcgcgatt gctttctttg tggtgtatcg tgccgttctg   13860
ttttgctgcg ctcgtcaacg ccaacagcaa cagcagctcc catttacagt tgatttacaa   13920
cttgacgcta tgtgagctga atggcacaga ttggctggct aacaaatttg attgggcagt   13980
ggagactttt gtcatctttc ccgtgttgac tcacattgtc tcctatggtg ccctcaccac   14040
cagccatttc cttgacacag tcggtctggt cactgtgtct accgccgggt tttatcacgg   14100
gcggtatgtc ttgagtagca tctacgcggt ctgtgccctg gctgcgttga tttgcttcgt   14160
cattaggttt gcgaagaact gcatgtcctg gcgctactca tgtaccagat ataccaactt   14220
tcttctggac actaagggca gactctatcg ttggcggtcg cccgtcatca tagagaaaag   14280
gggtaaagtt gaggtcgaag gtcatctgat cgacctcaaa agagttgtgc ttgatggttc   14340
cgtggcaacc cctttaacca gagtttcagc ggaacaatgg ggtcgtcctt agacgacttc   14400
tgccatgata gcacggctcc acaaaaggtg cttttggcgt tttctattac ctacacgcca   14460
gtgatgatat atgccctaaa ggtaagtcgc ggccgactgc tagggcttct gcaccttttg   14520 attttctga attgtgcttt caccttcggg tacatgacat tcgcgcactt tcagagcaca   14580
aataaggtcg cgctcactat gggagcagta gttgcactcc tttggggggt gtactcagcc   14640
atagaaacct ggaaattcat cacctccaga tgccgtttgt gcttgctagg ccgcaagtac   14700
```

```
attctggccc ctgccccacca cgttgaaagt gccgcaggct ttcatccgat tgcggcaaat    14760
gataaccacg catttgtcgt ccggcgtccc ggctccacta cggtcaacgg cacattggtg    14820
cccgggttga aaagcctcgt gttgggtggc agaaaagctg ttaaacaggg agtggtaaac    14880
cttgtcaaat atgccaaata caacggcaa gcagcagaag aaaaagaagg gggatggcca    14940
gccagtcaat cagctgtgcc agatgctggg taagatcatc gcccagcaaa accagtccag    15000
aggcaaggga ccgggaaaga aaataagaa gaaaaacccg gagaagcccc attttcctct    15060
agcgactgaa gatgacgtca gacatcactt taccccctagt gagcggcaat tgtgtctgtc    15120
gtcaatccag actgcctttta atcaaggcgc tggaacttgt accctgtcag attcagggag    15180
gataagttac actgtggagt ttagtttgcc gacgcatcat actgtgcgcc tgatccgcgt    15240
cacagcatca ccctcagcat gatgggctgg cattccttaa gcacctcagt gttagaattg    15300
gaagaatgtg tggtgaatgg cactgattgg cactgtgcct ctaagtcacc tattcaatta    15360
gggcgaccgt gtgggggtta agtttaattg gcgagaacca tgcggccgaa attaaaaaaa    15420
aaaaaaaaaa aaaaaaaaa aaaaaaaaa aaaaaa                               15456

<210> SEQ ID NO 2
<211> LENGTH: 540
<212> TYPE: DNA
<213> ORGANISM: Porcine reproductive and respiratory syndrome virus

<400> SEQUENCE: 2
atgtctggga tacttgatcg gtgcacgtgt accccaatg ccagggtgtt tatggcggag      60
ggccaagtct actgcacacg atgtctcagt gcacggtctc tccttcctct gaatctccaa     120
gttcctgagc tcggggtgct gggcctattt tacaggcccg aagagccact ccggtggacg     180
ttgccacgtg cattccccac tgtcgagtgc tcccccgccg gggcctgctg ctttctgcg     240 atctttccaa ttgcacgaat gaccagtgga aacctgaact ttcaacaaag aatggtgcgg     300
gtcgcagctg agctttacag agccggccag ctcacccctg cagtcttgaa ggctctacaa     360
gtttatgaac ggggttgccg ctggtacccc attgttggac ctgtccctgg agtggccgtt     420
ttcgccaact ccctacatgt gagtgataaa cctttcccgg agcaactca tgtgttaacc     480 aacctgccgc tcccgcagag gcccaagcct gaagactttt gcccctttga gtgtgctatg     540

<210> SEQ ID NO 3
<211> LENGTH: 180
<212> TYPE: PRT
<213> ORGANISM: Porcine reproductive and respiratory syndrome virus

<400> SEQUENCE: 3

Met Ser Gly Ile Leu Asp Arg Cys Thr Cys Thr Pro Asn Ala Arg Val
1               5                   10                  15

Phe Met Ala Glu Gly Gln Val Tyr Cys Thr Arg Cys Leu Ser Ala Arg
            20                  25                  30

Ser Leu Leu Pro Leu Asn Leu Gln Val Pro Glu Leu Gly Val Leu Gly
        35                  40                  45

Leu Phe Tyr Arg Pro Glu Glu Pro Leu Arg Trp Thr Leu Pro Arg Ala
    50                  55                  60

Phe Pro Thr Val Glu Cys Ser Pro Ala Gly Ala Cys Trp Leu Ser Ala
65                  70                  75                  80

Ile Phe Pro Ile Ala Arg Met Thr Ser Gly Asn Leu Asn Phe Gln Gln
                85                  90                  95
```

```
Arg Met Val Arg Val Ala Ala Glu Leu Tyr Arg Ala Gly Gln Leu Thr
            100                 105                 110

Pro Ala Val Leu Lys Ala Leu Gln Val Tyr Glu Arg Gly Cys Arg Trp
        115                 120                 125

Tyr Pro Ile Val Gly Pro Val Pro Gly Val Ala Val Phe Ala Asn Ser
    130                 135                 140

Leu His Val Ser Asp Lys Pro Phe Pro Gly Ala Thr His Val Leu Thr
145                 150                 155                 160

Asn Leu Pro Leu Pro Gln Arg Pro Lys Pro Glu Asp Phe Cys Pro Phe
                165                 170                 175

Glu Cys Ala Met
            180

<210> SEQ ID NO 4
<211> LENGTH: 609
<212> TYPE: DNA
<213> ORGANISM: Porcine reproductive and respiratory syndrome virus

<400> SEQUENCE: 4
gctgacgtct atgacattgg tcatgacgcc gtcatgtatg tggccgaagg gaaagtctcc    60
tgggcccctc gtggcgggga tgaagggaaa tttgaaactg tccccgagga gttgaagttg   120
attgcgaacc gactccacat ctccttcccg ccccaccacg cagtggacat gtctaagttt   180
gccttcatag cccctgggag tggtgtttcc atgcgggtcg agtgccaaca cggctgcctc   240
cccgctgaca ctgtccctga aggcaactgc tggtggcgct gtttgactt gctcccactg    300 gaagttcaga acaaagaaat tcgccatgct aaccaatttg gctatcagac caagcatggt   360
gtcgctggca gtacctaca gcggaggctg caagttaatg gtctccgagc agtgactgac    420
ccaaatggac ctatcgtcgt acagtatttc tctgttaagg agagctggat ccgccactta   480
agactggcgg aagaacctag cctccctggg tttgaggacc tcctcagaat aagggttgag   540
cccaacacgt cgccattggc tgacaaggat gagaaaatct ccggtttgg cagtcacaag     600 tggtacggt                                                           609

<210> SEQ ID NO 5
<211> LENGTH: 203
<212> TYPE: PRT
<213> ORGANISM: Porcine reproductive and respiratory syndrome virus

<400> SEQUENCE: 5

Ala Asp Val Tyr Asp Ile Gly His Asp Ala Val Met Tyr Val Ala Glu
1               5                   10                  15

Gly Lys Val Ser Trp Ala Pro Arg Gly Gly Asp Glu Gly Lys Phe Glu
            20                  25                  30

Thr Val Pro Glu Glu Leu Lys Leu Ile Ala Asn Arg Leu His Ile Ser
        35                  40                  45

Phe Pro Pro His His Ala Val Asp Met Ser Lys Phe Ala Phe Ile Ala
    50                  55                  60

Pro Gly Ser Gly Val Ser Met Arg Val Glu Cys Gln His Gly Cys Leu
65                  70                  75                  80

Pro Ala Asp Thr Val Pro Glu Gly Asn Cys Trp Trp Arg Leu Phe Asp
                85                  90                  95

Leu Leu Pro Leu Glu Val Gln Asn Lys Glu Ile Arg His Ala Asn Gln
            100                 105                 110

Phe Gly Tyr Gln Thr Lys His Gly Val Ala Gly Lys Tyr Leu Gln Arg
        115                 120                 125
```

```
Arg Leu Gln Val Asn Gly Leu Arg Ala Val Thr Asp Pro Asn Gly Pro
    130                 135                 140

Ile Val Val Gln Tyr Phe Ser Val Lys Glu Ser Trp Ile Arg His Leu
145                 150                 155                 160

Arg Leu Ala Glu Glu Pro Ser Leu Pro Gly Phe Glu Asp Leu Leu Arg
            165                 170                 175

Ile Arg Val Glu Pro Asn Thr Ser Pro Leu Ala Asp Lys Asp Glu Lys
            180                 185                 190

Ile Phe Arg Phe Gly Ser His Lys Trp Tyr Gly
            195                 200

<210> SEQ ID NO 6
<211> LENGTH: 3588
<212> TYPE: DNA
<213> ORGANISM: Porcine reproductive and respiratory syndrome virus

<400> SEQUENCE: 6
gctggaaaga gggcaaggaa agcacgctct ggtgcgactg ccacagtcgc tcaccgcgct     60
ttgcccgctc gtgaaaccca gcaggccaag aagcacgagg ttgccagcgc caacaaggct    120
gagcatctca gcactattc cccgcctgcc gacgggaact gtggttggca ctgcatttcc     180
gccatcgcca accggatggt gaattccaaa tttgaaacca cccttcccga agagtgaga    240 ccttcagatg actgggctac tgacgaggat cttgtgaata ccatccaaat cctcaggctc    300
cctgcggcct tggacaggaa cggtgcttgt gctagcgcca gtacgtgct taagctggaa     360 ggtgagcatt ggactgtctc tgtgaccct gggatgtccc cttctttgct ccccttgaa      420 tgtgttcagg gctgttgtga cataagggc ggtcttggtt ccccagatgc ggtcgaagtt     480
tccggatttg accctgcctg ccttgaccga ctggctgagg tgatgcactt gcctagcagt    540
gccatcccag ccgctctggc cgaaatgtcc ggcgacccca tcgtccggc ttccccggtc     600 accactgtgt ggactgtttc gcagttcttt gcccgtcaca gaggaggaga gcaccctgat    660
caggtgtgct tagggaaaat catcagcctt tgtcaggtga ttgaggaatg ctgctgttcc    720
cagaacaaaa ccaaccgggt caccccggaa gaggtcgcgg caaagattga ccagtacctc    780
cgtggtgcaa caagtcttga agaatgcttg gccaggcttg agagggctcg cccgccgagc    840
gcaatggaca cctcctttga ttggaatgtt gtgctccctg ggttgaggc ggcaactcag     900 acaaccaaac agccccatgt caaccagtgc cgcgctctgg tccctgtcgt gactcaagag    960
tctttggaca agactcggt ccctctgacc gccttctcgc tgtctaattg ctactaccct   1020
gcacaaggtg acgaggttcg tcaccgtgag aggctaaact ccgtgctctc taagttggag   1080
gaggttgttc gtgaggaata tgggctcacg ccaactggac ctggcccgcg acccgcactg   1140
ccgaacgggc tcgacgaact aaagaccag atggaggagg atctgctgaa actagtcaac   1200
gcccaggcaa cttcagaaat gatggcctgg gcagccgagc aggttgatct aaaagcttgg   1260
gtcaaaaact acccacggtg gacaccgcca ccccctccac caagagttca gcctcgaaaa   1320
acgaagtctg tcaagagctt gccagagaac aagcctgtcc ctgctccgcg caggaaggtc   1380
agatctgatt gtggcagccc gattttaatg ggcgacaatg tccctaacag ttgggaagat   1440
ttggctgttg gtgggcccct tgatctctcg acaccacccg agccgatgac acctctgagt   1500
gagcctgcac ttatgcccgc gttgcaacat atttctaggc cagtgacacc tttgagtgtg   1560
ccggccccaa ttcctgcacc gcgcagagct gtgtcccgac cggtgacgcc tcgagtgag    1620 ccaatttctg tgtctgcacc gcgacataaa tttcagcagg tggaagaagc gaatctggcg   1680
```

```
gcagcaacgc tgacgtacca ggacgaaccc ctagatttgt ctgcatcctc acagactgaa    1740
tatgaggctt ctcccctagc accactgcag aacatgggta ttctggaggt ggggggggcaa    1800
gaagctgagg aaattctgag tgaaatctcg gacataccga atgacatcaa ccctgcgcct    1860
gtgtcatcaa gcagctccct gtcaagcgtt aagatcacac gcccaaaata ctcagctcaa    1920
gccatcatcg actcgggcgg gccctgcagt gggcatctcc aaaaggaaaa agaagcatgc    1980
ctcagcatca tgcgtgaggc ttgtgatgcg actaagcttg gtgaccctgc cacgcaggaa    2040
tggctttctc gcatgtggga tagggtggac atgctgactt ggcgcaacac gtctgcttac    2100
caggcgtttc gcaccttaga tggcaggttt gagtttctcc caaagatgat actcgagaca    2160
ccgccgccct accgtgtggg gtttgtgatg ctgcctcaca cgcctgcacc ttccgtgggt    2220
gcggagagcg accttaccat tggttcagtc gccactgaag atgttccacg catcctcggg    2280
aaaatagaaa atgccggcga gatgaccaac cagggaccct ggcatcctc cgaggaagaa    2340
ccggcagacg accaacctgc caaagactcc cggatatcgt cgcggggtt tgacgagagc    2400
acagcagctc cgtccgcagg cacaggtggc gccggcttat ttactgattt gccaccttca    2460
gacggtgtag atgcggacgg ggggggggccg ttacagacgg taaaaagaa agctgaaagg    2520
ctcttcgacc aattgagccg tcaggttttt aacctcgtct cccatctccc tgttttcttc    2580
tcacacctct tcaaatctga cagtggttat tctccgggtg attggggttt tgcagctttt    2640
actctatttt gcctcttttt atgttacagt tacccattct ttggttttgc tccctcttg     2700
ggtgtgtttt ctgggtcttc tcggcgcgtg cgcatggggg ttttggctg ctggttggct    2760
tttgctgttg gtctgttcaa gcctgtgtcc gacccagtcg gcactgcttg tgagtttgat    2820
tcgccagagt gtaggaacgt ccttcattct ttgagcttc tcaaaccttg gaccctgtt     2880
cgcagccttg ttgtgggccc cgtcggtctc ggtcttgcca ttcttggcag gttactgggc    2940
ggggcacgct acatctggca ttttttgctt aggcttggca ttgttgcaga ctgtatcttg    3000
gctggagctt atgtgctttc tcaaggtagg tgtaaaaagt gctggggatc ttgtataaga    3060
actgctccta atgagatcgc ctttaacgtg ttccttttta cacgtgcgac caggtcgtca    3120
ctcatcgacc tgtgcgatcg gttttgtgcg ccaaaaggca tggaccccat tttcctcgcc    3180
actgggtggc gcgggtgctg gaccggccga agccccattg agcaaccctc tgaaaaaccc    3240
atcgcgtttg cccagttgga tgaaaagaag attacggcta ggactgtggt cgcccagcct    3300
tatgacccca accaagccgt aaagtgcttg cgggtgttac aggcgggtgg ggcgatggtg    3360
gctgaggcag tcccaaaagt ggtcaaggtt tccgctattc cattccgagc cccctttttt    3420
cccaccggag tgaaagttga ccctgagtgc aggatcgtgg ttgaccccga cactttcact    3480
acagctctcc ggtctggcta ctccaccaca aacctcgtcc ttggtgtggg gactttgcc     3540
cagctgaatg gattaaaaat caggcaaatt tccaagcctt caggagga                 3588
```

<210> SEQ ID NO 7
<211> LENGTH: 1196
<212> TYPE: PRT
<213> ORGANISM: Porcine reproductive and respiratory syndrome virus

<400> SEQUENCE: 7

```
Ala Gly Lys Arg Ala Arg Lys Ala Arg Ser Gly Ala Thr Ala Thr Val
 1               5                  10                  15

Ala His Arg Ala Leu Pro Ala Arg Glu Thr Gln Gln Ala Lys Lys His
             20                  25                  30
```

-continued

```
Glu Val Ala Ser Ala Asn Lys Ala Glu His Leu Lys His Tyr Ser Pro
             35                  40                  45

Pro Ala Asp Gly Asn Cys Gly Trp His Cys Ile Ser Ala Ile Ala Asn
 50                  55                  60

Arg Met Val Asn Ser Lys Phe Glu Thr Thr Leu Pro Glu Arg Val Arg
 65                  70                  75                  80

Pro Ser Asp Asp Trp Ala Thr Asp Glu Asp Leu Val Asn Thr Ile Gln
                 85                  90                  95

Ile Leu Arg Leu Pro Ala Ala Leu Asp Arg Asn Gly Ala Cys Ala Ser
            100                 105                 110

Ala Lys Tyr Val Leu Lys Leu Glu Gly Glu His Trp Thr Val Ser Val
            115                 120                 125

Thr Pro Gly Met Ser Pro Ser Leu Leu Pro Leu Glu Cys Val Gln Gly
            130                 135                 140

Cys Cys Glu His Lys Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Pro Asn Arg Pro Ala Ser Pro Val Thr Thr Val Trp Thr Val Ser Gln
            195                 200                 205

Phe Phe Ala Arg His Arg Gly Gly Glu His Pro Asp Gln Val Cys Leu
            210                 215                 220

Gly Lys Ile Ile Ser Leu Cys Gln Val Ile Glu Glu Cys Cys Cys Ser
225                 230                 235                 240

Gln Asn Lys Thr Asn Arg Val Thr Pro Glu Glu Val Ala Ala Lys Ile
                245                 250                 255

Asp Gln Tyr Leu Arg Gly Ala Thr Ser Leu Glu Glu Cys Leu Ala Arg
            260                 265                 270

Leu Glu Arg Ala Arg Pro Pro Ser Ala Met Asp Thr Ser Phe Asp Trp
            275                 280                 285

Asn Val Val Leu Pro Gly Val Glu Ala Ala Thr Gln Thr Thr Lys Gln
            290                 295                 300

Pro His Val Asn Gln Cys Arg Ala Leu Val Pro Val Thr Gln Glu
305                 310                 315                 320

Ser Leu Asp Lys Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
            340                 345                 350

Asn Ser Val Leu Ser Lys Leu Glu Glu Val Val Arg Glu Tyr Gly
            355                 360                 365

Leu Thr Pro Thr Gly Pro Gly Pro Arg Pro Ala Leu Pro Asn Gly Leu
            370                 375                 380

Asp Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
                405                 410                 415

Leu Lys Ala Trp Val Lys Asn Tyr Pro Arg Trp Thr Pro Pro Pro
            420                 425                 430

Pro Pro Arg Val Gln Pro Arg Lys Thr Lys Ser Val Lys Ser Leu Pro
            435                 440                 445

Glu Asn Lys Pro Val Pro Ala Pro Arg Arg Lys Val Arg Ser Asp Cys
```

```
            450                 455                 460
Gly Ser Pro Ile Leu Met Gly Asp Asn Val Pro Asn Ser Trp Glu Asp
465                 470                 475                 480

Leu Ala Val Gly Gly Pro Leu Asp Leu Ser Thr Pro Glu Pro Met
                485                 490                 495

Thr Pro Leu Ser Glu Pro Ala Leu Met Pro Ala Leu Gln His Ile Ser
                500                 505                 510

Arg Pro Val Thr Pro Leu Ser Val Pro Ala Pro Ile Pro Ala Pro Arg
                515                 520                 525

Arg Ala Val Ser Arg Pro Val Thr Pro Ser Ser Glu Pro Ile Ser Val
530                 535                 540

Ser Ala Pro Arg His Lys Phe Gln Gln Val Glu Glu Ala Asn Leu Ala
545                 550                 555                 560

Ala Ala Thr Leu Thr Tyr Gln Asp Glu Pro Leu Asp Leu Ser Ala Ser
                565                 570                 575

Ser Gln Thr Glu Tyr Glu Ala Ser Pro Leu Ala Pro Leu Gln Asn Met
                580                 585                 590

Gly Ile Leu Glu Val Gly Gly Gln Glu Ala Glu Ile Leu Ser Glu
                595                 600                 605

Ile Ser Asp Ile Pro Asn Asp Ile Asn Pro Ala Pro Val Ser Ser Ser
610                 615                 620

Ser Ser Leu Ser Ser Val Lys Ile Thr Arg Pro Lys Tyr Ser Ala Gln
625                 630                 635                 640

Ala Ile Ile Asp Ser Gly Gly Pro Cys Ser Gly His Leu Gln Lys Glu
                645                 650                 655

Lys Glu Ala Cys Leu Ser Ile Met Arg Glu Ala Cys Asp Ala Thr Lys
                660                 665                 670

Leu Gly Asp Pro Ala Thr Gln Glu Trp Leu Ser Arg Met Trp Asp Arg
                675                 680                 685

Val Asp Met Leu Thr Trp Arg Asn Thr Ser Ala Tyr Gln Ala Phe Arg
690                 695                 700

Thr Leu Asp Gly Arg Phe Glu Phe Leu Pro Lys Met Ile Leu Glu Thr
705                 710                 715                 720

Pro Pro Pro Tyr Pro Cys Gly Phe Val Met Leu Pro His Thr Pro Ala
                725                 730                 735

Pro Ser Val Gly Ala Glu Ser Asp Leu Thr Ile Gly Ser Val Ala Thr
                740                 745                 750

Glu Asp Val Pro Arg Ile Leu Gly Lys Ile Glu Asn Ala Gly Glu Met
                755                 760                 765

Thr Asn Gln Gly Pro Leu Ala Ser Ser Glu Glu Pro Ala Asp Asp
770                 775                 780

Gln Pro Ala Lys Asp Ser Arg Ile Ser Ser Arg Gly Phe Asp Glu Ser
785                 790                 795                 800

Thr Ala Ala Pro Ser Ala Gly Thr Gly Gly Ala Gly Leu Phe Thr Asp
                805                 810                 815

Leu Pro Pro Ser Asp Gly Val Asp Ala Asp Gly Gly Pro Leu Gln
                820                 825                 830

Thr Val Lys Lys Lys Ala Glu Arg Leu Phe Asp Gln Leu Ser Arg Gln
                835                 840                 845

Val Phe Asn Leu Val Ser His Leu Pro Val Phe Phe Ser His Leu Phe
850                 855                 860

Lys Ser Asp Ser Gly Tyr Ser Pro Gly Asp Trp Gly Phe Ala Ala Phe
865                 870                 875                 880
```

Thr Leu Phe Cys Leu Phe Leu Cys Tyr Ser Tyr Pro Phe Phe Gly Phe
                885                 890                 895

Ala Pro Leu Leu Gly Val Phe Ser Gly Ser Ser Arg Arg Val Arg Met
            900                 905                 910

Gly Val Phe Gly Cys Trp Leu Ala Phe Ala Val Gly Leu Phe Lys Pro
        915                 920                 925

Val Ser Asp Pro Val Gly Thr Ala Cys Glu Phe Asp Ser Pro Glu Cys
    930                 935                 940

Arg Asn Val Leu His Ser Phe Glu Leu Leu Lys Pro Trp Asp Pro Val
945                 950                 955                 960

Arg Ser Leu Val Val Gly Pro Val Gly Leu Gly Leu Ala Ile Leu Gly
                965                 970                 975

Arg Leu Leu Gly Gly Ala Arg Tyr Ile Trp His Phe Leu Leu Arg Leu
            980                 985                 990

Gly Ile Val Ala Asp Cys Ile Leu Ala Gly Ala Tyr Val Leu Ser Gln
        995                 1000                1005

Gly Arg Cys Lys Lys Cys Trp Gly Ser Cys Ile Arg Thr Ala Pro
    1010                1015                1020

Asn Glu Ile Ala Phe Asn Val Phe Pro Phe Thr Arg Ala Thr Arg
    1025                1030                1035

Ser Ser Leu Ile Asp Leu Cys Asp Arg Phe Cys Ala Pro Lys Gly
    1040                1045                1050

Met Asp Pro Ile Phe Leu Ala Thr Gly Trp Arg Gly Cys Trp Thr
    1055                1060                1065

Gly Arg Ser Pro Ile Glu Gln Pro Ser Glu Lys Pro Ile Ala Phe
    1070                1075                1080

Ala Gln Leu Asp Glu Lys Lys Ile Thr Ala Arg Thr Val Val Ala
    1085                1090                1095

Gln Pro Tyr Asp Pro Asn Gln Ala Val Lys Cys Leu Arg Val Leu
    1100                1105                1110

Gln Ala Gly Gly Ala Met Val Ala Glu Ala Val Pro Lys Val Val
    1115                1120                1125

Lys Val Ser Ala Ile Pro Phe Arg Ala Pro Phe Phe Pro Thr Gly
    1130                1135                1140

Val Lys Val Asp Pro Glu Cys Arg Ile Val Val Asp Pro Asp Thr
    1145                1150                1155

Phe Thr Thr Ala Leu Arg Ser Gly Tyr Ser Thr Thr Asn Leu Val
    1160                1165                1170

Leu Gly Val Gly Asp Phe Ala Gln Leu Asn Gly Leu Lys Ile Arg
    1175                1180                1185

Gln Ile Ser Lys Pro Ser Gly Gly
    1190                1195

<210> SEQ ID NO 8
<211> LENGTH: 690
<212> TYPE: DNA
<213> ORGANISM: Porcine reproductive and respiratory syndrome virus

<400> SEQUENCE: 8
ggcccacacc tcattgctgc cctgcatgtt gcctgctcga tggcgttgca catgcttgct      60
gggatttatg taactgcagt ggggtcttgc ggtaccggca ccaacgatcc gtggtgcact     120
aacccgtttg ccgtccctgg ctacggacct ggctctctct gcacgtccag attgtgcatc     180
tcccaacatg gccttaccct gcccttgaca gcacttgtgg caggattcgg tcttcaggaa     240

```
attgccttgg ttgttttgat tttcgtttcc atcggaggca tggctcacag gttgagttgc    300
aaggctgata tgctgtgcgt tttacttgca atcgccagct atgtttgggt acccccttacc   360 tggttgcttt gtgtgtttcc ttgctggttg cgctggttct ctttgcaccc cctcaccatc    420
ctatggttgg tgttttctt gatttctgta aatatgcctt caggaatctt ggccgtggtg     480
ttgttggttt ctctttggct tctaggtcgt tatactaatg ttgctggtct tgtcaccccc    540
tatgacattc atcattacac cagtggcccc cgcggtgttg ccgccttggc taccgcacca    600
gatgggacct acttggccgc tgtccgccgc gctgcgttga ctggccgcac catgctgttt    660
accccgtctc agcttgggtc ccttcttgag                                     690

<210> SEQ ID NO 9
<211> LENGTH: 230
<212> TYPE: PRT
<213> ORGANISM: Porcine reproductive and respiratory syndrome virus

<400> SEQUENCE: 9

Gly Pro His Leu Ile Ala Ala Leu His Val Ala Cys Ser Met Ala Leu
1               5                   10                  15

His Met Leu Ala Gly Ile Tyr Val Thr Ala Val Gly Ser Cys Gly Thr
            20                  25                  30

Gly Thr Asn Asp Pro Trp Cys Thr Asn Pro Phe Ala Val Pro Gly Tyr
        35                  40                  45

Gly Pro Gly Ser Leu Cys Thr Ser Arg Leu Cys Ile Ser Gln His Gly
    50                  55                  60

Leu Thr Leu Pro Leu Thr Ala Leu Val Ala Gly Phe Gly Leu Gln Glu
65                  70                  75                  80

Ile Ala Leu Val Val Leu Ile Phe Val Ser Ile Gly Gly Met Ala His
                85                  90                  95

Arg Leu Ser Cys Lys Ala Asp Met Leu Cys Val Leu Leu Ala Ile Ala
            100                 105                 110

Ser Tyr Val Trp Val Pro Leu Thr Trp Leu Leu Cys Val Phe Pro Cys
        115                 120                 125

Trp Leu Arg Trp Phe Ser Leu His Pro Leu Thr Ile Leu Trp Leu Val
    130                 135                 140

Phe Phe Leu Ile Ser Val Asn Met Pro Ser Gly Ile Leu Ala Val Val
145                 150                 155                 160

Leu Leu Val Ser Leu Trp Leu Leu Gly Arg Tyr Thr Asn Val Ala Gly
                165                 170                 175

Leu Val Thr Pro Tyr Asp Ile His His Tyr Thr Ser Gly Pro Arg Gly
            180                 185                 190

Val Ala Ala Leu Ala Thr Ala Pro Asp Gly Thr Tyr Leu Ala Ala Val
        195                 200                 205

Arg Arg Ala Ala Leu Thr Gly Arg Thr Met Leu Phe Thr Pro Ser Gln
    210                 215                 220

Leu Gly Ser Leu Leu Glu
225                 230

<210> SEQ ID NO 10
<211> LENGTH: 612
<212> TYPE: DNA
<213> ORGANISM: Porcine reproductive and respiratory syndrome virus

<400> SEQUENCE: 10
ggtgctttca gaactcaaaa gccctcactg aacaccgtca atgtggtcgg gtcctccatg    60
```

| | |
|---|---:|
| ggctctggcg gggtgttcac catcgacggg aaaattaagt gcgtaactgc cgcacatgtc | 120 |
| cttacgggta attcagctag ggtttccggg gtcggcttca atcaaatgct tgactttgat | 180 |
| gtaaagggg acttcgccat agctgattgc ccgaattggc aagggctgc tcccaagacc | 240 |
| caattctgca aggatggatg gactggccgt gcctattggc tgacatcctc tggcgtcgaa | 300 |
| cccggtgtca ttgggaatgg attcgccttc tgcttcaccg cgtgcggcga ttccgggtcc | 360 |
| ccagtgatca ccgaagccgg tgagcttgtc ggcgttcaca caggatcaaa caaacaagga | 420 |
| ggaggcattg tcacgcgccc ctcaggccag ttttgtaatg tggcacccat caagctgagc | 480 |
| gaattaagtg aattctttgc tggacctaag gtcccgctcg gtgatgtgaa ggttggcagc | 540 |
| cacataatta aagacataag cgaggtgcct tcagatcttt gcgccttgct tgctgccaaa | 600 |
| cccgaactgg aa | 612 |

<210> SEQ ID NO 11
<211> LENGTH: 204
<212> TYPE: PRT
<213> ORGANISM: Porcine reproductive and respiratory syndrome virus

<400> SEQUENCE: 11

Gly Ala Phe Arg Thr Gln Lys Pro Ser Leu Asn Thr Val Asn Val Val
1               5                   10                  15
Gly Ser Ser Met Gly Ser Gly Gly Val Phe Thr Ile Asp Gly Lys Ile
            20                  25                  30
Lys Cys Val Thr Ala Ala His Val Leu Thr Gly Asn Ser Ala Arg Val
        35                  40                  45
Ser Gly Val Gly Phe Asn Gln Met Leu Asp Phe Asp Val Lys Gly Asp
    50                  55                  60
Phe Ala Ile Ala Asp Cys Pro Asn Trp Gln Gly Ala Ala Pro Lys Thr
65                  70                  75                  80
Gln Phe Cys Lys Asp Gly Trp Thr Gly Arg Ala Tyr Trp Leu Thr Ser
                85                  90                  95
Ser Gly Val Glu Pro Gly Val Ile Gly Asn Gly Phe Ala Phe Cys Phe
            100                 105                 110
Thr Ala Cys Gly Asp Ser Gly Ser Pro Val Ile Thr Glu Ala Gly Glu
        115                 120                 125
Leu Val Gly Val His Thr Gly Ser Asn Lys Gln Gly Gly Gly Ile Val
    130                 135                 140
Thr Arg Pro Ser Gly Gln Phe Cys Asn Val Ala Pro Ile Lys Leu Ser
145                 150                 155                 160
Glu Leu Ser Glu Phe Phe Ala Gly Pro Lys Val Pro Leu Gly Asp Val
                165                 170                 175
Lys Val Gly Ser His Ile Ile Lys Asp Ile Ser Glu Val Pro Ser Asp
            180                 185                 190
Leu Cys Ala Leu Leu Ala Ala Lys Pro Glu Leu Glu
        195                 200

<210> SEQ ID NO 12
<211> LENGTH: 510
<212> TYPE: DNA
<213> ORGANISM: Porcine reproductive and respiratory syndrome virus

<400> SEQUENCE: 12

| | |
|---|---:|
| ggaggcctct ccaccgtcca acttctgtgt gtgttttcc tcctgtggag aatgatggga | 60 |
| catgcctgga cgcccttggt tgctgtgggt tttttatct tgaatgaggt tctcccagct | 120 |

```
gtcctggtcc ggagtgtttt ctcctttgga atgtttgtgc tatcttggct cacaccatgg    180
tctgcgcaag ttctgatgat caggcttcta acagcagctc ttaacaggaa cagatggtca    240
cttgcctttt acagcctcgg tgcagtgacc ggttttgtcg cagatcttgc ggcaactcag    300
gggcatccgt tgcaggcagt gatgaattta agcacctatg ccttcctgcc tcggatgatg    360
gttgtgacct caccagtccc agtgattgcg tgtggtgttg tgcacctcct tgccataatt    420
ttgtacttgt ttaagtaccg ttgcctgcac aatgtccttg ttggcgatgg agtgttctct    480
gcggctttct tcttgcgata ctttgccgag                                     510
```

<210> SEQ ID NO 13
<211> LENGTH: 170
<212> TYPE: PRT
<213> ORGANISM: Porcine reproductive and respiratory syndrome virus

<400> SEQUENCE: 13

Gly Gly Leu Ser Thr Val Gln Leu Leu Cys Val Phe Phe Leu Leu Trp
1               5                   10                  15

Arg Met Met Gly His Ala Trp Thr Pro Leu Val Ala Val Gly Phe Phe
                20                  25                  30

Ile Leu Asn Glu Val Leu Pro Ala Val Leu Val Arg Ser Val Phe Ser
            35                  40                  45

Phe Gly Met Phe Val Leu Ser Trp Leu Thr Pro Trp Ser Ala Gln Val
    50                  55                  60

Leu Met Ile Arg Leu Leu Thr Ala Ala Leu Asn Arg Asn Arg Trp Ser
65                  70                  75                  80

Leu Ala Phe Tyr Ser Leu Gly Ala Val Thr Gly Phe Val Ala Asp Leu
                85                  90                  95

Ala Ala Thr Gln Gly His Pro Leu Gln Ala Val Met Asn Leu Ser Thr
            100                 105                 110

Tyr Ala Phe Leu Pro Arg Met Met Val Val Thr Ser Pro Val Pro Val
        115                 120                 125

Ile Ala Cys Gly Val Val His Leu Leu Ala Ile Ile Leu Tyr Leu Phe
    130                 135                 140

Lys Tyr Arg Cys Leu His Asn Val Leu Val Gly Asp Gly Val Phe Ser
145                 150                 155                 160

Ala Ala Phe Phe Leu Arg Tyr Phe Ala Glu
                165                 170

<210> SEQ ID NO 14
<211> LENGTH: 48
<212> TYPE: DNA
<213> ORGANISM: Porcine reproductive and respiratory syndrome virus

<400> SEQUENCE: 14
ggaaagttga gggaaggggt gtcgcaatcc tgcgggatga atcatgag                  48

<210> SEQ ID NO 15
<211> LENGTH: 16
<212> TYPE: PRT
<213> ORGANISM: Porcine reproductive and respiratory syndrome virus

<400> SEQUENCE: 15

Gly Lys Leu Arg Glu Gly Val Ser Gln Ser Cys Gly Met Asn His Glu
1               5                   10                  15

<210> SEQ ID NO 16

```
<211> LENGTH: 777
<212> TYPE: DNA
<213> ORGANISM: Porcine reproductive and respiratory syndrome virus

<400> SEQUENCE: 16
tcactgactg gtgccctcgc tatgagactc aatgacgagg acttggattt ccttacgaaa      60
tggactgatt ttaagtgctt tgtttctgcg tccaacatga ggaatgcagc gggccaattc     120
atcgaggctg cctatgctaa agcacttaga gtagaacttg cccagttggt gcaggttgat     180
aaggttcgag gtactttggc caaacttgaa gcttttgctg ataccgtggc accccaactc     240
tcgcccggtg acattgttgt tgctcttggc cacacgcctg ttggcagtat cttcgaccta     300
aaggttggta gcaccaagca taccctccaa gccattgaga ccagagtcct tgccgggtcc     360
aaaatgaccg tggcgcgcgt cgttgaccca accccacgc cccaccgc acccgtgccc      420 atcccctcc accgaaagt tctggagaat ggccccaacg cctgggggga tgaggaccgt     480
ttgaataaga agaagaggcg caggatgaa gccgtcggca tctttgttat gggcgggaag     540
aagtaccaga attttggga caagaattcc ggtgatgtgt tttatgagga ggtccatgat     600
aacacagatg cgtgggagtg cctcagagtt ggcgaccctg ccgactttga ccctgagaag     660
ggaactctgt gtgggcatac caccattgaa gataaggctt acaatgtcta cgcctccccaa     720 tctggcaaga agttcctggt ccccgtcaac ccagagagcg aagagccca atgggaa         777

<210> SEQ ID NO 17
<211> LENGTH: 259
<212> TYPE: PRT
<213> ORGANISM: Porcine reproductive and respiratory syndrome virus

<400> SEQUENCE: 17

Ser Leu Thr Gly Ala Leu Ala Met Arg Leu Asn Asp Glu Asp Leu Asp
1               5                   10                  15

Phe Leu Thr Lys Trp Thr Asp Phe Lys Cys Phe Val Ser Ala Ser Asn
            20                  25                  30

Met Arg Asn Ala Ala Gly Gln Phe Ile Glu Ala Ala Tyr Ala Lys Ala
        35                  40                  45

Leu Arg Val Glu Leu Ala Gln Leu Val Gln Val Asp Lys Val Arg Gly
    50                  55                  60

Thr Leu Ala Lys Leu Glu Ala Phe Ala Asp Thr Val Ala Pro Gln Leu
65                  70                  75                  80

Ser Pro Gly Asp Ile Val Val Ala Leu Gly His Thr Pro Val Gly Ser
                85                  90                  95

Ile Phe Asp Leu Lys Val Gly Ser Thr Lys His Thr Leu Gln Ala Ile
            100                 105                 110

Glu Thr Arg Val Leu Ala Gly Ser Lys Met Thr Val Ala Arg Val Val
        115                 120                 125

Asp Pro Thr Pro Thr Pro Pro Ala Pro Val Pro Ile Pro Leu Pro
    130                 135                 140

Pro Lys Val Leu Glu Asn Gly Pro Asn Ala Trp Gly Asp Glu Asp Arg
145                 150                 155                 160

Leu Asn Lys Lys Lys Arg Arg Arg Met Glu Ala Val Gly Ile Phe Val
                165                 170                 175

Met Gly Gly Lys Lys Tyr Gln Lys Phe Trp Asp Lys Asn Ser Gly Asp
            180                 185                 190

Val Phe Tyr Glu Glu Val His Asp Asn Thr Asp Ala Trp Glu Cys Leu
        195                 200                 205
```

```
Arg Val Gly Asp Pro Ala Asp Phe Asp Pro Glu Lys Gly Thr Leu Cys
    210                 215                 220

Gly His Thr Thr Ile Glu Asp Lys Ala Tyr Asn Val Tyr Ala Ser Pro
225                 230                 235                 240

Ser Gly Lys Lys Phe Leu Val Pro Val Asn Pro Glu Ser Gly Arg Ala
                245                 250                 255

Gln Trp Glu

<210> SEQ ID NO 18
<211> LENGTH: 138
<212> TYPE: DNA
<213> ORGANISM: Porcine reproductive and respiratory syndrome virus

<400> SEQUENCE: 18
gctgcaaagc tttccgtgga gcaggccctt ggcatgatga atgtcgacgg tgaactgaca      60
gccaaagaac tggagaaact gaaaagaata attgacaaac tccagggcct gactaaggag     120
cagtgtttaa actgctag                                                   138

<210> SEQ ID NO 19
<211> LENGTH: 45
<212> TYPE: PRT
<213> ORGANISM: Porcine reproductive and respiratory syndrome virus

<400> SEQUENCE: 19

Ala Ala Lys Leu Ser Val Glu Gln Ala Leu Gly Met Met Asn Val Asp
1               5                   10                  15

Gly Glu Leu Thr Ala Lys Glu Leu Glu Lys Leu Lys Arg Ile Ile Asp
            20                  25                  30

Lys Leu Gln Gly Leu Thr Lys Glu Gln Cys Leu Asn Cys
        35                  40                  45

<210> SEQ ID NO 20
<211> LENGTH: 1917
<212> TYPE: DNA
<213> ORGANISM: Porcine reproductive and respiratory syndrome virus

<400> SEQUENCE: 20
gccgccagcg gcttgacccg ctgtggtcgc ggcggcttgg ttgttactga cagcggta       60 aaaatagtca atttcacaa ccggaccttc accctaggac ctgtgaattt aaaagtggcc     120
agtgaggttg agctaaaaga cgcggtcgag cacaaccaac acccggttgc aagaccggtt    180
gatggtggtg ttgtgctcct cgctccgca gttccttcgc ttatagacgt cttgatctcc    240
ggtgctgatg catctcccaa gttactcgcc cgccacgggc cgggaaacac tgggatcgat    300
ggcacgcttt gggattttga ggccgaagcc accaaagagg aaatcgcact cagtgcgcaa    360
ataatacagg cttgtgacat taggcgcggc gacgcacctg aaattggtct cccttacaag    420
ctgtaccctg ttaggggcaa ccctgagcgg gtaaaaggag ttttgcagaa tacaaggttt    480
ggagacatac cttacaaaac ccccagtgac actggaagcc agtgcacgc ggctgcctgc    540 ctcacgccca atgccactcc ggtgactgat gggcgctccg tcttggccac gaccatgccc    600
tccggttttg agttgtatgt accgaccatt ccagcgtctg tccttgatta tcttgattct    660
aggcctgact gccccaaaca gttgacagag cacggctgtg aggatgccgc attgagagac    720
ctctccaagt atgacttgtc cacccaaggc tttgttttgc ctggagttct tcgccttgtg    780
cgtaagtacc tgtttgccca tgtgggtaag tgccgcccg ttcatcggcc ttccacttac    840
cctgccaaga attctatggc tggaataaat gggaacaggt ttccaaccaa ggacattcag    900
```

```
agcgtccctg aaatcgacgt tctgtgcgca caggccgtgc gagaaaactg gcaaactgtt   960
accccttgta ccctcaagaa acagtattgc gggaagaaga agactaggac aatactcggc  1020
accaataact tcattgcgct ggcccaccgg gcagcgttga gtggtgtcac ccagggcttc  1080
atgaaaaagg cgtttaactc gcccatcgcc ctcgggaaaa acaaatttaa ggagctacag  1140
actccggtct tgggcaggtg ccttgaagct gatcttgcat cctgcgatcg atccacacct  1200
gcaattgtcc gctggtttgc cgccaatctt ctttatgaac ttgcctgtgc tgaagagcat  1260
ctaccgtcgt acgtgctgaa ctgctgccac gacttactgg tcacgcagtc cggcgcagtg  1320
actaagagag gtggcctgtc gtctggcgac ccgatcactt ctgtgtccaa caccatttac  1380
agcttggtga tatatgcaca gcacatggtg ctcagttact ttaaaagtgg tcaccccat   1440 ggccttctgt ttctacaaga ccagctaaag tttgaggaca tgctcaaggt tcaacccctg  1500
atcgtctatt cggacgacct cgtgctgtat gccgagtctc ccaccatgcc aaactaccac  1560
tggtgggttg aacatctgaa cctgatgctg gttttcaga cggacccaaa gaagacagcc  1620
ataacagact cgccatcatt tctaggctgt aggataataa atgggcgcca gctagtcccc  1680
aaccgtgaca ggattctcgc ggccctcgcc taccacatga aggcgagcaa tgtttctgaa  1740
tactacgcct cggcggctgc aatactcatg gacagctgtg cttgtttgga gtatgatcct  1800
gaatggtttg aagaacttgt ggttggaata gcgcagtgcg cccgcaagga cggctacagc  1860
tttcccggcc cgccgttctt cttgtccatg tgggaaaaac tcaggtccaa ttatgag     1917

<210> SEQ ID NO 21
<211> LENGTH: 639
<212> TYPE: PRT
<213> ORGANISM: Porcine reproductive and respiratory syndrome virus

<400> SEQUENCE: 21

Ala Ala Ser Gly Leu Thr Arg Cys Gly Arg Gly Gly Leu Val Val Thr
1               5                   10                  15

Glu Thr Ala Val Lys Ile Val Lys Phe His Asn Arg Thr Phe Thr Leu
            20                  25                  30

Gly Pro Val Asn Leu Lys Val Ala Ser Glu Val Glu Leu Lys Asp Ala
        35                  40                  45

Val Glu His Asn Gln His Pro Val Ala Arg Pro Val Asp Gly Gly Val
    50                  55                  60

Val Leu Leu Arg Ser Ala Val Pro Ser Leu Ile Asp Val Leu Ile Ser
65                  70                  75                  80

Gly Ala Asp Ala Ser Pro Lys Leu Leu Ala Arg His Gly Pro Gly Asn
                85                  90                  95

Thr Gly Ile Asp Gly Thr Leu Trp Asp Phe Glu Ala Glu Ala Thr Lys
            100                 105                 110

Glu Glu Ile Ala Leu Ser Ala Gln Ile Ile Gln Ala Cys Asp Ile Arg
        115                 120                 125

Arg Gly Asp Ala Pro Glu Ile Gly Leu Pro Tyr Lys Leu Tyr Pro Val
    130                 135                 140

Arg Gly Asn Pro Glu Arg Val Lys Gly Val Leu Gln Asn Thr Arg Phe
145                 150                 155                 160

Gly Asp Ile Pro Tyr Lys Thr Pro Ser Asp Thr Gly Ser Pro Val His
                165                 170                 175

Ala Ala Ala Cys Leu Thr Pro Asn Ala Thr Pro Val Thr Asp Gly Arg
            180                 185                 190
```

```
Ser Val Leu Ala Thr Thr Met Pro Ser Gly Phe Glu Leu Tyr Val Pro
            195                 200                 205

Thr Ile Pro Ala Ser Val Leu Asp Tyr Leu Asp Ser Arg Pro Asp Cys
210                 215                 220

Pro Lys Gln Leu Thr Glu His Gly Cys Glu Asp Ala Ala Leu Arg Asp
225                 230                 235                 240

Leu Ser Lys Tyr Asp Leu Ser Thr Gln Gly Phe Val Leu Pro Gly Val
                245                 250                 255

Leu Arg Leu Val Arg Lys Tyr Leu Phe Ala His Val Gly Lys Cys Pro
            260                 265                 270

Pro Val His Arg Pro Ser Thr Tyr Pro Ala Lys Asn Ser Met Ala Gly
        275                 280                 285

Ile Asn Gly Asn Arg Phe Pro Thr Lys Asp Ile Gln Ser Val Pro Glu
290                 295                 300

Ile Asp Val Leu Cys Ala Gln Ala Val Arg Glu Asn Trp Gln Thr Val
305                 310                 315                 320

Thr Pro Cys Thr Leu Lys Lys Gln Tyr Cys Gly Lys Lys Lys Thr Arg
                325                 330                 335

Thr Ile Leu Gly Thr Asn Asn Phe Ile Ala Leu Ala His Arg Ala Ala
            340                 345                 350

Leu Ser Gly Val Thr Gln Gly Phe Met Lys Lys Ala Phe Asn Ser Pro
        355                 360                 365

Ile Ala Leu Gly Lys Asn Lys Phe Lys Glu Leu Gln Thr Pro Val Leu
370                 375                 380

Gly Arg Cys Leu Glu Ala Asp Leu Ala Ser Cys Asp Arg Ser Thr Pro
385                 390                 395                 400

Ala Ile Val Arg Trp Phe Ala Ala Asn Leu Leu Tyr Glu Leu Ala Cys
                405                 410                 415

Ala Glu Glu His Leu Pro Ser Tyr Val Leu Asn Cys Cys His Asp Leu
            420                 425                 430

Leu Val Thr Gln Ser Gly Ala Val Thr Lys Arg Gly Gly Leu Ser Ser
        435                 440                 445

Gly Asp Pro Ile Thr Ser Val Ser Asn Thr Ile Tyr Ser Leu Val Ile
450                 455                 460

Tyr Ala Gln His Met Val Leu Ser Tyr Phe Lys Ser Gly His Pro His
465                 470                 475                 480

Gly Leu Leu Phe Leu Gln Asp Gln Leu Lys Phe Glu Asp Met Leu Lys
                485                 490                 495

Val Gln Pro Leu Ile Val Tyr Ser Asp Asp Leu Val Leu Tyr Ala Glu
            500                 505                 510

Ser Pro Thr Met Pro Asn Tyr His Trp Trp Val Glu His Leu Asn Leu
        515                 520                 525

Met Leu Gly Phe Gln Thr Asp Pro Lys Lys Thr Ala Ile Thr Asp Ser
530                 535                 540

Pro Ser Phe Leu Gly Cys Arg Ile Ile Asn Gly Arg Gln Leu Val Pro
545                 550                 555                 560

Asn Arg Asp Arg Ile Leu Ala Ala Leu Ala Tyr His Met Lys Ala Ser
                565                 570                 575

Asn Val Ser Glu Tyr Tyr Ala Ser Ala Ala Ile Leu Met Asp Ser
            580                 585                 590

Cys Ala Cys Leu Glu Tyr Asp Pro Glu Trp Phe Glu Glu Leu Val Val
        595                 600                 605

Gly Ile Ala Gln Cys Ala Arg Lys Asp Gly Tyr Ser Phe Pro Gly Pro
```

```
                 610                 615                 620
Pro Phe Phe Leu Ser Met Trp Glu Lys Leu Arg Ser Asn Tyr Glu
625                 630                 635

<210> SEQ ID NO 22
<211> LENGTH: 1323
<212> TYPE: DNA
<213> ORGANISM: Porcine reproductive and respiratory syndrome virus

<400> SEQUENCE: 22
gggaagaagt ccagagtgtg cgggtactgc ggggcccogg ccccgtacgc cactgcctgt      60
ggcctcgacg tctgtattta ccacacccac ttccaccagc attgtccagt cataatctgg     120
tgtggccatc cagcgggttc tggttcttgt agtgagtgca aaccccccct agggaaaggc     180
acaagccctc tagatgaggt gttggaacaa gtcccgtata gcctccacg accgtaatc      240
atgcatgtgg agcagggtct caccectctt gacccaggca gataccagac tcgccgcgga     300
ttagtctccg ttaggcgtgg catcagggga aatgaagttg acctaccaga cggtgattat     360
gctagcaccg ccttgctccc cacttgtaaa gagatcaaca tggtcgctgt cgcttctaat     420
gtgttgcgca gcaggttcat catcggtcca cccggtgctg ggaaaacata ctggctcctt     480
caacaggtcc aggatggtga tgtcatttac acaccaactc atcagaccat gcttgacatg     540
attaaggctt tggggacgtg ccggttcaac gtcccggcag gcacaacgct gcaattccct     600
gccccctccc gtaccggccc gtgggttcgc atcctggccg gcggttggtg tcctggcaag     660
aattccttcc tggatgaagc agcgtattgt aatcaccttg atgtcttgag gcttcttagc     720
aaaactaccc tcacctgtct gggagacttc aaacaactcc acccagtggg ttttgattct     780
cattgctatg tttttgacat catgcctcag actcaactga agaccatctg gaggtttgga     840
cagaatatct gtgatgccat tcagccagat tacagggaca aacttgtgtc catggtcaac     900
acaaccogtg taacctacgt ggaaaaacct gtcaagtatg gcaagtcct cacccccttac     960
cacagggacc gagaggacgg cgccatcaca attgactcca gtcaaggcgc acatttgat    1020
gtggttacat tgcatttgcc cactaaagat tcactcaaca ggcaaagagc ccttgttgct    1080
atcaccaggg caagacatgc tatctttgtg tatgacccac acaggcaact gcagagcatg    1140
tttgatcttc ctgcaaaagg cacacccgtc aacctcgccg tgcaccgtga cgagcagctg    1200
atcgtgctag atagaaataa caagaatgca cgttgctc aggctctagg caatggggat    1260
aaattcaggg ccacagacaa gcgcgttgta gattctctcc gcgccatttg tgcagatcta    1320
gaa                                                                  1323

<210> SEQ ID NO 23
<211> LENGTH: 441
<212> TYPE: PRT
<213> ORGANISM: Porcine reproductive and respiratory syndrome virus

<400> SEQUENCE: 23

Gly Lys Lys Ser Arg Val Cys Gly Tyr Cys Gly Ala Pro Ala Pro Tyr
1               5                   10                  15

Ala Thr Ala Cys Gly Leu Asp Val Cys Ile Tyr His Thr His Phe His
            20                  25                  30

Gln His Cys Pro Val Ile Ile Trp Cys Gly His Pro Ala Gly Ser Gly
        35                  40                  45

Ser Cys Ser Glu Cys Lys Pro Pro Leu Gly Lys Gly Thr Ser Pro Leu
    50                  55                  60
```

```
Asp Glu Val Leu Glu Gln Val Pro Tyr Lys Pro Arg Thr Val Ile
 65                  70                  75                  80

Met His Val Glu Gln Gly Leu Thr Pro Leu Asp Pro Gly Arg Tyr Gln
                 85                  90                  95

Thr Arg Arg Gly Leu Val Ser Val Arg Arg Gly Ile Arg Gly Asn Glu
            100                 105                 110

Val Asp Leu Pro Asp Gly Asp Tyr Ala Ser Thr Ala Leu Leu Pro Thr
        115                 120                 125

Cys Lys Glu Ile Asn Met Val Ala Val Ala Ser Asn Val Leu Arg Ser
    130                 135                 140

Arg Phe Ile Ile Gly Pro Pro Gly Ala Gly Lys Thr Tyr Trp Leu Leu
145                 150                 155                 160

Gln Gln Val Gln Asp Gly Asp Val Ile Tyr Thr Pro Thr His Gln Thr
                165                 170                 175

Met Leu Asp Met Ile Lys Ala Leu Gly Thr Cys Arg Phe Asn Val Pro
            180                 185                 190

Ala Gly Thr Thr Leu Gln Phe Pro Ala Pro Ser Arg Thr Gly Pro Trp
        195                 200                 205

Val Arg Ile Leu Ala Gly Gly Trp Cys Pro Gly Lys Asn Ser Phe Leu
    210                 215                 220

Asp Glu Ala Ala Tyr Cys Asn His Leu Asp Val Leu Arg Leu Leu Ser
225                 230                 235                 240

Lys Thr Thr Leu Thr Cys Leu Gly Asp Phe Lys Gln Leu His Pro Val
                245                 250                 255

Gly Phe Asp Ser His Cys Tyr Val Phe Asp Ile Met Pro Gln Thr Gln
            260                 265                 270

Leu Lys Thr Ile Trp Arg Phe Gly Gln Asn Ile Cys Asp Ala Ile Gln
        275                 280                 285

Pro Asp Tyr Arg Asp Lys Leu Val Ser Met Val Asn Thr Thr Arg Val
    290                 295                 300

Thr Tyr Val Glu Lys Pro Val Lys Tyr Gly Gln Val Leu Thr Pro Tyr
305                 310                 315                 320

His Arg Asp Arg Glu Asp Gly Ala Ile Thr Ile Asp Ser Ser Gln Gly
                325                 330                 335

Ala Thr Phe Asp Val Val Thr Leu His Leu Pro Thr Lys Asp Ser Leu
            340                 345                 350

Asn Arg Gln Arg Ala Leu Val Ala Ile Thr Arg Ala Arg His Ala Ile
        355                 360                 365

Phe Val Tyr Asp Pro His Arg Gln Leu Gln Ser Met Phe Asp Leu Pro
370                 375                 380

Ala Lys Gly Thr Pro Val Asn Leu Ala Val His Arg Asp Glu Gln Leu
385                 390                 395                 400

Ile Val Leu Asp Arg Asn Asn Lys Glu Cys Thr Val Ala Gln Ala Leu
                405                 410                 415

Gly Asn Gly Asp Lys Phe Arg Ala Thr Asp Lys Arg Val Val Asp Ser
            420                 425                 430

Leu Arg Ala Ile Cys Ala Asp Leu Glu
        435                 440

<210> SEQ ID NO 24
<211> LENGTH: 669
<212> TYPE: DNA
<213> ORGANISM: Porcine reproductive and respiratory syndrome virus

<400> SEQUENCE: 24
```

```
gggtcgagct ctccgctccc caaggtcgca cacaacttgg gatttattt ctcacctgat    60 ttgacacagt ttgctaaact cccggtagaa cttgcacccc actggcccgt ggtgacaacc   120
cagaacaatg aaaagtggcc agaccggctg gttgccagcc ttcgccctat ccataaatat   180
agccgcgcgt gcatcggtgc cggctatatg gtgggcccct cggtgtttct aggcacccct   240
ggggttgtgt catactatct cacaaaattt gttaagggcg aggctcaagt gcttccggag   300
acagtcttca gcaccggccg aattgaggta gattgccggg agtatcttga tgatcgggag   360
cgagaagttg ctgagtccct cccacatgcc ttcattggcg acgtcaaagg cactaccgtt   420
ggaggatgtc accatgtcac ctccaaatac cttccgcgct tccttcccaa ggaatcagtt   480
gcggtagtcg ggtttcaag ccccgggaaa gccgcaaaag cagtttgcac attaacagat   540
gtgtacctcc agaccttga agcttacctc cacccagaga cccagtccaa gtgctggaaa   600
atgatgttgg acttcaagga agttcgactg atggtctgga agacaaaac ggcctatttt   660 caacttgaa                                                           669

<210> SEQ ID NO 25
<211> LENGTH: 223
<212> TYPE: PRT
<213> ORGANISM: Porcine reproductive and respiratory syndrome virus

<400> SEQUENCE: 25

Gly Ser Ser Ser Pro Leu Pro Lys Val Ala His Asn Leu Gly Phe Tyr
1               5                   10                  15

Phe Ser Pro Asp Leu Thr Gln Phe Ala Lys Leu Pro Val Glu Leu Ala
            20                  25                  30

Pro His Trp Pro Val Val Thr Thr Gln Asn Asn Glu Lys Trp Pro Asp
        35                  40                  45

Arg Leu Val Ala Ser Leu Arg Pro Ile His Lys Tyr Ser Arg Ala Cys
    50                  55                  60

Ile Gly Ala Gly Tyr Met Val Gly Pro Ser Val Phe Leu Gly Thr Pro
65                  70                  75                  80

Gly Val Val Ser Tyr Tyr Leu Thr Lys Phe Val Lys Gly Glu Ala Gln
                85                  90                  95

Val Leu Pro Glu Thr Val Phe Ser Thr Gly Arg Ile Glu Val Asp Cys
            100                 105                 110

Arg Glu Tyr Leu Asp Asp Arg Glu Arg Glu Val Ala Glu Ser Leu Pro
        115                 120                 125

His Ala Phe Ile Gly Asp Val Lys Gly Thr Thr Val Gly Gly Cys His
    130                 135                 140

His Val Thr Ser Lys Tyr Leu Pro Arg Phe Leu Pro Lys Glu Ser Val
145                 150                 155                 160

Ala Val Val Gly Val Ser Ser Pro Gly Lys Ala Ala Lys Ala Val Cys
                165                 170                 175

Thr Leu Thr Asp Val Tyr Leu Pro Asp Leu Glu Ala Tyr Leu His Pro
            180                 185                 190

Glu Thr Gln Ser Lys Cys Trp Lys Met Met Leu Asp Phe Lys Glu Val
        195                 200                 205

Arg Leu Met Val Trp Lys Asp Lys Thr Ala Tyr Phe Gln Leu Glu
    210                 215                 220

<210> SEQ ID NO 26
<211> LENGTH: 462
<212> TYPE: DNA
```

<213> ORGANISM: Porcine reproductive and respiratory syndrome virus

<400> SEQUENCE: 26

```
ggccgccatt tcacctggta tcagcttgca agctatgcct cgtacatccg agttcctgtt      60
aactctacgg tgtatttgga cccctgcatg ggccctgccc tttgcaacag aagagttgtc     120
gggtccactc attgggggc tgacctcgca gtcaccccctt atgattatgg tgccaaaatc     180
attctgtcta gtgcatacca tggtgaaatg cctcctgggt acaaaatcct ggcgtgcgcg     240
gagttctcgc ttgacgatcc agtgaggtac aaacacacct gggggtttga atcggataca     300
gcgtatctgt acgagttcac cggaaacggt gaggactggg aggattacaa tgatgcgttt     360
cgtgcgcgcc agaaagggaa aatttataag gccactgcca ccagcatgag gtttcatttt     420
cccccgggcc ctgtcattga accaactttg ggcctgaatt ga                        462
```

<210> SEQ ID NO 27
<211> LENGTH: 153
<212> TYPE: PRT
<213> ORGANISM: Porcine reproductive and respiratory syndrome virus

<400> SEQUENCE: 27

```
Gly Arg His Phe Thr Trp Tyr Gln Leu Ala Ser Tyr Ala Ser Tyr Ile
1               5                   10                  15
Arg Val Pro Val Asn Ser Thr Val Tyr Leu Asp Pro Cys Met Gly Pro
            20                  25                  30
Ala Leu Cys Asn Arg Arg Val Val Gly Ser Thr His Trp Gly Ala Asp
        35                  40                  45
Leu Ala Val Thr Pro Tyr Asp Tyr Gly Ala Lys Ile Ile Leu Ser Ser
    50                  55                  60
Ala Tyr His Gly Glu Met Pro Pro Gly Tyr Lys Ile Leu Ala Cys Ala
65                  70                  75                  80
Glu Phe Ser Leu Asp Asp Pro Val Arg Tyr Lys His Thr Trp Gly Phe
                85                  90                  95
Glu Ser Asp Thr Ala Tyr Leu Tyr Glu Phe Thr Gly Asn Gly Glu Asp
            100                 105                 110
Trp Glu Asp Tyr Asn Asp Ala Phe Arg Ala Arg Gln Lys Gly Lys Ile
        115                 120                 125
Tyr Lys Ala Thr Ala Thr Ser Met Arg Phe His Phe Pro Pro Gly Pro
    130                 135                 140
Val Ile Glu Pro Thr Leu Gly Leu Asn
145                 150
```

<210> SEQ ID NO 28
<211> LENGTH: 771
<212> TYPE: DNA
<213> ORGANISM: Porcine reproductive and respiratory syndrome virus

<400> SEQUENCE: 28

```
atgaaatggg ggctatgcaa agccttttg acaaaattgg ccaacttttt gtggatgctt      60
tcacggaatt tttggtgtcc attgttgata tcatcatatt tttggccatt tgtttggct     120
tcaccatcgc cggttggctg gtggtctttt gcatcagatt ggtttgctcc gcggtactcc     180
gtgcgcgccc taccattcac cctgagcaat tacagaagat cctatgaggc ctttctttct     240
cagtgccggg tggacattcc cacctgggga actaaacatc ccttggggat gctttggcac     300
cataaggtgt caaccctgat tgatgaaatg gtgtcgcgtc gaatgtaccg catcatggaa     360
aaagcaggac aggctgcctg gaaacaggtg gtgagcgagg ctacgctgtc tcgcattagt     420
```

```
ggtttggatg tggtggctca ttttcagcat cttgccgcca ttgaagccga gacctgtaaa      480
tatttggcct ctcggctgcc catgctacac aacctgcgca tgacagggtc aaatgtaacc      540
atagtgtata atagtacttt gaatcaggtg tttgctattt ttccaacccc tggttcccgg      600
ccaaagcttc atgattttca gcaatggcta atagctgtgc attcctccat attttcctct      660
gttgcagctt cttgtactct ttttgttgtg ctgtggttgc ggattccaat gctacgtact      720
gtttttggtt tccactggtt aggggcaatt tttccttcga actcacagtg a               771
```

<210> SEQ ID NO 29
<211> LENGTH: 256
<212> TYPE: PRT
<213> ORGANISM: Porcine reproductive and respiratory syndrome virus

<400> SEQUENCE: 29

```
Met Lys Trp Gly Leu Cys Lys Ala Phe Leu Thr Lys Leu Ala Asn Phe
1               5                   10                  15

Leu Trp Met Leu Ser Arg Asn Phe Trp Cys Pro Leu Leu Ile Ser Ser
            20                  25                  30

Tyr Phe Trp Pro Phe Cys Leu Ala Ser Pro Ser Pro Val Gly Trp Trp
        35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
65                  70                  75                  80

Gln Cys Arg Val Asp Ile Pro Thr Trp Gly Thr Lys His Pro Leu Gly
                85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Gly Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Ile Pro Met Leu Arg Thr
225                 230                 235                 240

Val Phe Gly Phe His Trp Leu Gly Ala Ile Phe Pro Ser Asn Ser Gln
                245                 250                 255
```

<210> SEQ ID NO 30
<211> LENGTH: 765
<212> TYPE: DNA
<213> ORGANISM: Porcine reproductive and respiratory syndrome virus

<400> SEQUENCE: 30

```
atggctaata gctgtgcatt cctccatatt ttcctctgtt gcagcttctt gtactctttt       60
```

-continued

```
tgttgtgctg tggttgcgga ttccaatgct acgtactgtt tttggtttcc actggttagg      120
ggcaattttt ccttcgaact cacagtgaat tacacggtgt gtccaccttg cctcacccgg      180
caagcagccg ctgagatcta cgaacccggc aggtctcttt ggtgcaggat agggcatgac      240
cgatgtaggg aggacgatca tgacgaacta gggttcatgg ttccgcctgg cctctccagc      300
gaaggccact tgaccagtgt ttacgcctgg ttggcgttcc tgtccttcag ctacacggcc      360
cagttccatc ccgagatatt tgggataggg aatgtgagtc aagtttatgt tgacatcaag      420
caccaattca tctgcgccga acatgacggg cagaacgcca ccttgcctcg ccatgacaac      480
atttcagccg tgtttcagac ctactaccaa catcaggtcg acggcggcaa ttggtttcac      540
ctagaatggc tgcgcccctt ctttttcctct tggttggttt taaatgtttc gtggtttctc      600
aggcgttcgc ctgcaagcca tgtttcagtt cgagtctttc agacatcaag accaacacca      660
ccgcagcagc aagctttgtt gtcctccaag acatcagctg ccttaggcat ggcgactcgt      720
cctctgaggc gattcgcaaa agctctcagt gccgcacggc gatag                     765
```

<210> SEQ ID NO 31
<211> LENGTH: 254
<212> TYPE: PRT
<213> ORGANISM: Porcine reproductive and respiratory syndrome virus

<400> SEQUENCE: 31

```
Met Ala Asn Ser Cys Ala Phe Leu His Ile Phe Leu Cys Cys Ser Phe
1               5                   10                  15

Leu Tyr Ser Phe Cys Cys Ala Val Val Ala Asp Ser Asn Ala Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Ala
    50                  55                  60

Glu Ile Tyr Glu Pro Gly Arg Ser Leu Trp Cys Arg Ile Gly His Asp
65                  70                  75                  80

Arg Cys Arg Glu Asp Asp His Asp Glu Leu Gly Phe Met Val Pro Pro
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Gln Val Tyr Val Asp Ile Lys His Gln Phe Ile
    130                 135                 140

Cys Ala Glu His Asp Gly Gln Asn Ala Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Phe Gln Thr Ser Arg Pro Thr Pro Gln Gln Gln
    210                 215                 220

Ala Leu Leu Ser Ser Lys Thr Ser Ala Ala Leu Gly Met Ala Thr Arg
225                 230                 235                 240

Pro Leu Arg Arg Phe Ala Lys Ala Leu Ser Ala Ala Arg Arg
                245                 250
```

<210> SEQ ID NO 32
<211> LENGTH: 537
<212> TYPE: DNA
<213> ORGANISM: Porcine reproductive and respiratory syndrome virus

<400> SEQUENCE: 32

```
atggctgcgc cccttctttt cctcttggtt ggttttaaat gtttcgtggt ttctcaggcg    60
ttcgcctgca agccatgttt cagttcgagt ctttcagaca tcaagaccaa caccaccgca   120
gcagcaagct tgttgtcct ccaagacatc agctgcctta ggcatggcga ctcgtcctct   180
gaggcgattc gcaaaagctc tcagtgccgc acggcgatag ggacacccgt gtacatcacc   240
atcacagcca atgtgacaga tgagaattat ttacattctt ctgatctcct catgctttct   300
tcttgccttt tctatgcttc tgagatgagt gaaaagggat caaggtggt atttggcaat   360
gtgtcaggca tcgtggctgt gtgtgtcaac tttaccagct acgtccaaca tgtcaaggag   420
tttacccaac gctccttggt ggtcgaccat gtgcggctgc ttcatttcat gacacctgag   480
accatgaggt gggcaaccgt tttagcctgt cttttgcca ttctgttggc aatttga     537
```

<210> SEQ ID NO 33
<211> LENGTH: 178
<212> TYPE: PRT
<213> ORGANISM: Porcine reproductive and respiratory syndrome virus

<400> SEQUENCE: 33

```
Met Ala Ala Pro Leu Leu Phe Leu Leu Val Gly Phe Lys Cys Phe Val
1               5                   10                  15

Val Ser Gln Ala Phe Ala Cys Lys Pro Cys Phe Ser Ser Ser Leu Ser
            20                  25                  30

Asp Ile Lys Thr Asn Thr Thr Ala Ala Ala Ser Phe Val Val Leu Gln
        35                  40                  45

Asp Ile Ser Cys Leu Arg His Gly Asp Ser Ser Ser Glu Ala Ile Arg
    50                  55                  60

Lys Ser Ser Gln Cys Arg Thr Ala Ile Gly Thr Pro Val Tyr Ile Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

<210> SEQ ID NO 34
<211> LENGTH: 603
<212> TYPE: DNA
<213> ORGANISM: Porcine reproductive and respiratory syndrome virus

<400> SEQUENCE: 34

```
atgttgggga aatgcttgac cgcgggctgt tgctcgcgat tgctttcttt gtggtgtatc    60
```

```
gtgccgttct gttttgctgc gctcgtcaac gccaacagca acagcagctc ccatttacag    120
ttgatttata acttgacgct atgtgagctg aatggcacag attggctggc taacaaattt    180
gattgggcag tggagacttt tgtcatcttt cccgtgttga ctcacattgt ctcctatggt    240
gccctcacca ccagccattt ccttgacaca gtcggtctgg tcactgtgtc taccgccggg    300
ttttatcacg gcggtatgt cttgagtagc atctacgcgg tctgtgccct ggctgcgttg    360
atttgcttcg tcattaggtt tgcgaagaac tgcatgtcct ggcgctactc atgtaccaga    420
tataccaact tcttctggga cactaagggc agactctatc gttggcggtc gcccgtcatc    480
atagagaaaa ggggtaaagt tgaggtcgaa ggtcatctga tcgacctcaa aagagttgtg    540
cttgatggtt ccgtggcaac ccctttaacc agagtttcag cggaacaatg gggtcgtcct    600
tag                                                                  603

<210> SEQ ID NO 35
<211> LENGTH: 200
<212> TYPE: PRT
<213> ORGANISM: Porcine reproductive and respiratory syndrome virus

<400> SEQUENCE: 35

Met Leu Gly Lys Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Phe Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Pro
        195                 200

<210> SEQ ID NO 36
<211> LENGTH: 525
<212> TYPE: DNA
<213> ORGANISM: Porcine reproductive and respiratory syndrome virus

<400> SEQUENCE: 36
atggggtcgt ccttagacga cttctgccat gatagcacgg ctccacaaaa ggtgcttttg     60
gcgttttcta ttacctacac gccagtgatg atatatgccc taaaggtaag tcgcggccga    120
```

```
ctgctagggc ttctgcacct tttgattttt ctgaattgtg ctttcacctt cgggtacatg    180
acattcgcgc actttcagag cacaaataag gtcgcgctca ctatgggagc agtagttgca    240
ctcctttggg gggtgtactc agccatagaa acctggaaat tcatcacctc cagatgccgt    300
ttgtgcttgc taggccgcaa gtacattctg gcccctgccc accacgttga agtgccgca     360 ggctttcatc cgattgcggc aaatgataac cacgcatttg tcgtccggcg tcccggctcc    420
actacggtca acggcacatt ggtgcccggg ttgaaaagcc tcgtgttggg tggcagaaaa    480
gctgttaaac agggagtggt aaaccttgtc aaatatgcca aataa                    525

<210> SEQ ID NO 37
<211> LENGTH: 174
<212> TYPE: PRT
<213> ORGANISM: Porcine reproductive and respiratory syndrome virus

<400> SEQUENCE: 37

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Ala His
    50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 38
<211> LENGTH: 372
<212> TYPE: DNA
<213> ORGANISM: Porcine reproductive and respiratory syndrome virus

<400> SEQUENCE: 38
atgccaaata caacggcaa gcagcagaag aaaaagaagg gggatggcca gccagtcaat     60
cagctgtgcc agatgctggg taagatcatc gcccagcaaa accagtccag aggcaaggga    120
ccgggaaaga aaataagaa gaaaaacccg agaagcccc atttttcctct agcgactgaa     180 gatgacgtca gacatcactt tacccctagt gagcggcaat gtgtctgtc gtcaatccag     240 actgccttta atcaaggcgc tggaacttgt accctgtcag attcagggag ataagttac     300 actgtggagt ttagttttgcc gacgcatcat actgtgcgcc tgatccgcgt cacagcatca    360
ccctcagcat ga                                                        372
```

<210> SEQ ID NO 39
<211> LENGTH: 123
<212> TYPE: PRT
<213> ORGANISM: Porcine reproductive and respiratory syndrome virus

<400> SEQUENCE: 39

```
Met Pro Asn Asn Gly Lys Gln Gln Lys Lys Lys Gly Asp Gly
1               5                   10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Lys Lys Lys
            35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

<210> SEQ ID NO 40
<211> LENGTH: 156
<212> TYPE: DNA
<213> ORGANISM: Porcine reproductive and respiratory syndrome virus

<400> SEQUENCE: 40

```
atgttcaagt atgttgggga aatgcttgac cgcgggctgt tgctcgcgat tgctttcttt      60
gtggtgtatc gtgccgttct gttttgctgc gctcgtcaac gccaacagca acagcagctc     120
ccatttacag ttgatttaca acttgacgct atgtga                                156
```

<210> SEQ ID NO 41
<211> LENGTH: 51
<212> TYPE: PRT
<213> ORGANISM: Porcine reproductive and respiratory syndrome virus

<400> SEQUENCE: 41

```
Met Phe Lys Tyr Val Gly Glu Met Leu Asp Arg Gly Leu Leu Leu Ala
1               5                   10                  15

Ile Ala Phe Phe Val Val Tyr Arg Ala Val Leu Phe Cys Cys Ala Arg
                20                  25                  30

Gln Arg Gln Gln Gln Gln Leu Pro Phe Thr Val Asp Leu Gln Leu
            35                  40                  45

Asp Ala Met
    50
```

<210> SEQ ID NO 42
<211> LENGTH: 222
<212> TYPE: DNA
<213> ORGANISM: Porcine reproductive and respiratory syndrome virus

<400> SEQUENCE: 42

```
atgggggcta tgcaaagcct ttttgacaaa attggccaac ttttttgtgga tgctttcacg      60 gaattttttgg tgtccattgt tgatatcatc atattttttgg ccattttgtt tggcttcacc    120
atcgccggtt ggctggtggt cttttgcatc agattggttt gctccgcggt actccgtgcg    180
```

```
cgccctacca ttcaccctga gcaattacag aagatcctat ga                    222
```

<210> SEQ ID NO 43
<211> LENGTH: 73
<212> TYPE: PRT
<213> ORGANISM: Porcine reproductive and respiratory syndrome virus

<400> SEQUENCE: 43

```
Met Gly Ala Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
            20                  25                  30

Leu Ala Ile Leu Phe Gly Phe Thr Ile Ala Gly Trp Leu Val Val Phe
        35                  40                  45

Cys Ile Arg Leu Val Cys Ser Ala Val Leu Arg Ala Arg Pro Thr Ile
    50                  55                  60

His Pro Glu Gln Leu Gln Lys Ile Leu
65                  70
```